United States Patent [19]
Soller et al.

[11] Patent Number: 5,813,403
[45] Date of Patent: Sep. 29, 1998

[54] OPTICAL MEASUREMENT OF TISSUE PH

[76] Inventors: Babs R. Soller, 15 Franklin Cir., Northboro, Mass. 01532; Ronald H. Micheels, 176 Jennie Dugan Rd., Concord, Mass. 01742

[21] Appl. No.: 555,102

[22] Filed: Nov. 8, 1995

[51] Int. Cl.⁶ .................................................. A61B 5/000
[52] U.S. Cl. ............................................................ 128/633
[58] Field of Search ................................. 128/633, 634, 128/664, 665, 666; 356/39–41, 300, 306, 319, 326

[56] References Cited

U.S. PATENT DOCUMENTS

| | | | |
|---|---|---|---|
| 4,033,330 | 7/1977 | Willis et al. | |
| 4,041,932 | 8/1977 | Fostick. | |
| 5,337,745 | 8/1994 | Benaron | 128/664 |
| 5,355,880 | 10/1994 | Thomas et al. | 128/664 |
| 5,435,309 | 7/1995 | Thomas et al. | 128/633 |
| 5,441,053 | 8/1995 | Lodder et al. | 128/634 |
| 5,494,032 | 2/1996 | Robinson et al. | 128/633 |
| 5,522,389 | 6/1996 | Fischer et al. | 128/634 |

OTHER PUBLICATIONS

Benaron, "Optical Biopsy and Imaging Advance Medical Care", Laser Focus World, 79–87, Jan. 1994.

Benesch et al., "Equations for the Spectrophotometric Analysis of Hemoglobin Mixtures", Anal Biochem 55:245–248, 1973.

Drennen et al., "Near–Infrared Spectrometric Determination of Hydrogen Ion, Glucose, and Human Serum Albumin in a Simulated Biological Matrix", Spectroscopy, 6:28–34, 1991.

Dunn et al., "Experimental and Chemical Use of pH Monitoring of Free Tissue Transfers", Anals of Plastic Surgery, 30:1–7, 1993.

Hampson et al., "Near Infrared Monitoring of Human Skeletal Muscle Oxygenation During Forearm Ischemia", American Physiological Society, 2449–2453, 1988.

Parsons et al., "Dynamic Mechanisms of Cardiac Oxygenation During Brief Ischemia and Reperfusion", American Physiological Society, 1477–1485, 1990.

Reeves, "Influence of pH, Ionic Strength, and Physical State on the Near–Infrared Spectra of Model Compounds" J. of AOAC International, 77:814–820, 1994.

Robinson et al., "Noninvasive Glucose Monitoring in Diabetic Patients: A Preliminary Evaluation" Clinical Chemistry, 38:1618–1622, 1992.

Snell et al., "A Convenient Spectroscopic Method for the Estimation of Hemoglobin Concentrations in Cell–Free Solutions", J. Biochem & Biophys Methods 17:25–34, 1988.

Sobezynski, "Diode Arrays May Light Up Compact Spectrometers", Laser Focus World, 75–81, Mar. 1995.

Wait, "Fiber–Optic Sensors for Continuous Clinical Monitoring", Proceedings of the IEEE, 80:903–911, 1992.

Ward et al., "Post–Prandial Blood Glucose Determination by Quantitative Mid–Infrared Spectroscopy", Applied Spectroscopy, 46:959–965, 1992.

Vari et al., "Blood Perfusion and pH Monitoring in Organs Via Optical Biopsy", Am. Soc. for Lasers in Surgery and Medicine Supplement 7:3, Abstract 10, 1995 (Apr.).

*Primary Examiner*—Jennifer Bahr
*Assistant Examiner*—Bryan K. Yarnell
*Attorney, Agent, or Firm*—Fish & Richardson P.C.

[57] ABSTRACT

The invention provides an optical method and apparatus for determining the pH of a tissue. The method includes the step of first irradiating the tissue with optical radiation. The radiation may first pass through skin covering the tissue of interest, or may irradiate the tissue directly. Radiation reflected from the tissue is then collected to determine a reflection spectrum. pH is then determined by comparing this spectrum to a mathematical model relating optical properties to pH of the tissue.

54 Claims, 15 Drawing Sheets

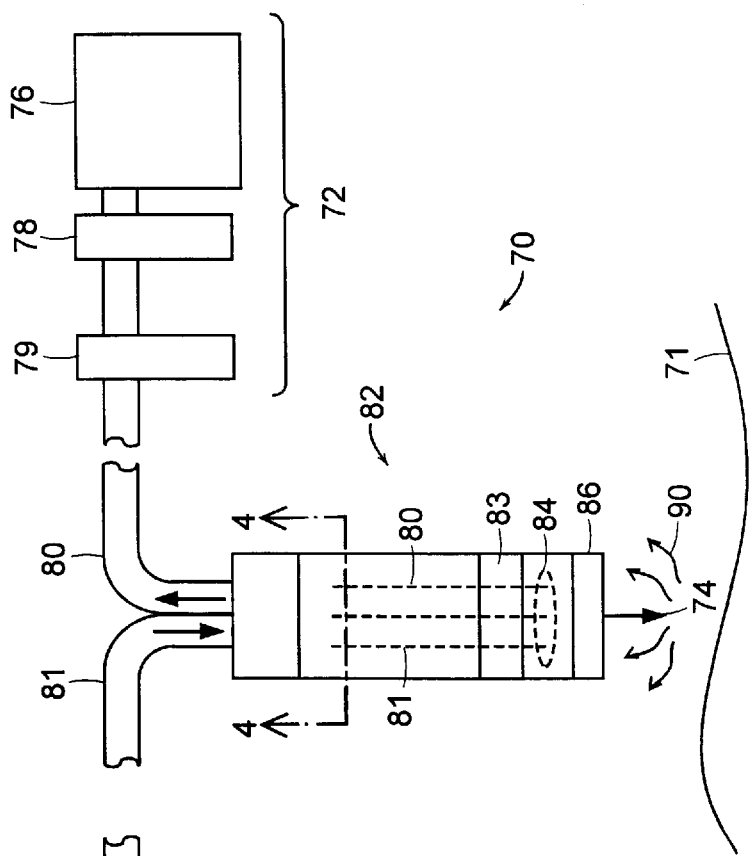
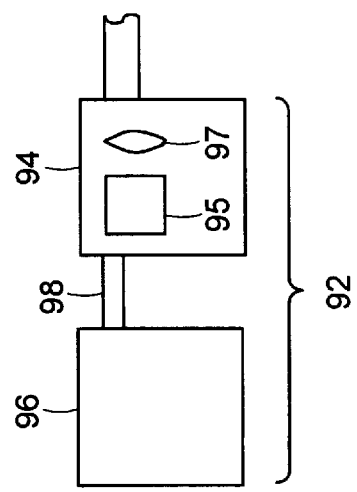
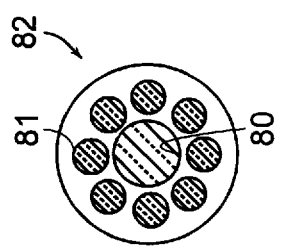

SUMMARY OF MODEL STATISTICS

| EXPT NO. | PROBE | λ (nm) | DECREASING pH | | | INCREASING pH | | | COMBINED UP & DOWN | | |
|---|---|---|---|---|---|---|---|---|---|---|---|
| | | | FACTORS | $R^2$ | RMSD | FACTORS | $R^2$ | RMSD | FACTORS | $R^2$ | RMSD |
| R3J | ANGLED | 500-1000 | 1 | .90 | .03 | N/A | N/A | N/A | N/A | N/A | N/A |
| R4J | ANGLED | 500-1000 | 1 | .82 | .06 | 3 | .32 | .13 | NONE | NONE | NONE |
| R4J SKIN | ANGLED | 500-1000 | 2 | .92 | .02 | N/A | N/A | N/A | N/A | N/A | N/A |
| R5J | COLLINEAR | 500-1000 | 6 | .95 | .05 | 4 | .41 | .21 | 11 | .78 | .11 |
| R6J | COLLINEAR | 500-1000 | NONE | NONE | NONE | 3 | .94 | .03 | 2 | .22 | .10 |
| R7J | ANGLED (30°) | 1100-1400 | 5 | .79 | .09 | 3 | .81 | .11 | 6 | .87 | .09 |
| R8J | COLLINEAR | 500-1000 | 2 | .76 | .09 | NONE | NONE | NONE | 7 | .63 | .10 |
| R9J | ANGLED (60°) | 400-1250 | 4 | .99 | .02 | 3 | .99 | .03 | 10 | .98 | .03 |
| R9J | ANGLED (60°) | 700-1250 | | | | | | | 6 | .98 | .03 |
| R9J SKIN | ANGLED (60°) | 400-1100 | 4 | .99 | .02 | N/A | N/A | N/A | N/A | N/A | N/A |
| R9J SKIN | ANGLED (60°) | 1100-2000 | 2 | .94 | .04 | N/A | N/A | N/A | N/A | N/A | N/A |

FIG. 14

TABLE III. COMPARISON OF MODEL STATISTICS FOR TWO DIFFERENT WAVELENGTH REGIONS

| EXPERIMENT NUMBER | FULL RANGE $R^2$ | 700-1100 nm $R^2$ | FULL RANGE RMDS | 700-1100 nm RMDS |
|---|---|---|---|---|
| R10J RIGHT, SKIN | 0.923 | 0.988 | 0.030 | 0.011 |
| R11J RIGHT, SKIN | 0.986 | 0.996 | 0.023 | 0.014 |
| R12J RIGHT, SKIN | 0.978 | 0.984 | 0.015 | 0.013 |
| R13J RIGHT, SKIN | 0.979 | 0.972 | 0.024 | 0.026 |
| R14J RIGHT, SKIN | 0.993 | 0.994 | 0.011 | 0.010 |
| R14J LEFT, SKIN | 0.974 | 0.968 | 0.016 | 0.019 |

FIG. 17A

TABLE IV. PREDICTED pH FOR DEEP MUSCLE TISSUE COVERED WITH A SKIN FLAP: 700-1100 nm

| EXPERIMENT NUMBER | pH RANGE | NUMBER OF POINTS PREDICTED | AVERAGE ERROR OF PREDICTION (ACTUAL - PREDICTED pH) |
|---|---|---|---|
| R10J | 6.98-7.25 | 3 | -0.003 pH UNITS |
| R11J | 6.53-7.41 | 4 | -0.012 pH UNITS |
| R12J | 7.02-7.35 | 3 | -0.011 pH UNITS |
| R13J | 6.77-7.33 | 4 | +0.011 pH UNITS |
| R14JR | 6.74-7.16 | 3 | -0.009 pH UNITS |
| R14JL | 6.41-6.75 | 3 | -0.014 pH UNITS |

FIG. 17B

OPTICAL MEASUREMENT OF TISSUE PH

STATEMENT AS TO FEDERALLY SPONSORED RESEARCH

The invention described herein was made in the performance of work funded in part by Small Business Innovative Research Grant No. DAMD17-95C-5042 sponsored by the U.S. Army. The Government has certain rights in this invention.

BACKGROUND

This invention relates to measurement of pH.

Interruption of blood flow to a tissue impedes oxygen delivery and results in a condition called ischemia. The duration and extent of ischemia is directly related to the tissue's viability. Even as blood flow is stopped, adenosine triphosphate (ATP) can be hydrolyzed in the tissue's cells to produce energy through anaerobic metabolism; the by-products of this process are hydrogen ions and lactic acid. Thus, when blood flow is interrupted, both lactic acid and hydrogen ions accumulate, resulting in a decrease in the pH of both the cell and the interstitial fluid surrounding the cell.

It is critical during many surgical procedures to determine both the rate of blood flow to a tissue and the degree of ischemia. A quantitative measurement of ischemia often indicates the appropriate clinical response for treating the tissue. In trauma applications, for example, the degree of ischemic damage is a primary factor in determining whether or not to amputate a tissue or organ. Blood flow is carefully monitored when a patient undergoes an operation to ensure the accuracy and safety of the procedure. In open-heart surgery, for example, normal blood flow to the heart is deliberately stopped to facilitate the operation; measures must be taken to restore blood flow if the heart becomes ischemic. Similarly, restoration of blood flow is carefully monitored during plastic or reconstructive surgical procedures in which tissue or organs are reattached or restored.

Current assessments of tissue ischemia are typically made by a physician's qualitative observation of skin or organ color. As would be expected, the non-quantitative nature of this assessment can result in an inaccurate diagnosis. Blood flow can be estimated using ultrasonic and temperature-based measurements. However, temperature-based measurements are often unreliable and suffer in accuracy. Moreover, it is often difficult to attach temperature-measuring probes to the patient. Ultrasonic methods, such as Doppler-based imaging, suffer from low spatial resolution and can provide inaccurate measurements concerning the direction of blood flow.

pH of a tissue can be measured to determine blood flow, blood flow history, and ischemia. For example, while normal perfused tissue has a pH in the range of 7.1 to 7.3, a tissue deprived of blood for a time period of about 4–6 hours will have a pH of about 5.8–6.3.

Existing pH sensors are typically electrodes which directly contact the patient's tissue. While providing accurate measurements of pH for short periods of time, these sensors are often prone to drift, thereby reducing the long term reliability of the measurement. Electrode insertion, especially repeated insertion, can also damage the tissue. Another invasive pH sensor is the tonometer, an instrument which determines the pH of the gut by measuring $CO_2$ pressure therein. Fiber-optic pH sensors are invasive devices featuring chemical compounds exhibiting pH-dependent optical properties coated onto the fiber's tip. During operation, the fiber is inserted directly into a sample. Reflectance spectra of the compound are taken using radiation coupled into the fiber to determine the sample's pH.

SUMMARY

In general, in one aspect, the invention provides an optical method for determining the pH of a tissue disposed underneath a covering tissue, e.g., skin, of a patient. The method includes the step of first irradiating the tissue with optical radiation which is not substantially absorbed by the covering tissue. Here, "not substantially absorbed" means that at least 10% of the incident radiation is propagated through the covering tissue. This radiation thus propagates through the covering tissue and irradiates the underlying tissue. Radiation reflected from the tissue and through the covering tissue is then collected to determine a reflection spectrum. pH is determined by processing this spectrum and a mathematical model relating optical properties to pH of the tissue.

In another aspect, the method provides a method for determining the pH of a sample tissue without a covering tissue. The method features the steps of irradiating the sample tissue with optical radiation; collecting radiation reflected from the sample tissue to determine a reflection spectrum; and then analyzing the reflection spectrum by processing the spectrum and a mathematical model relating optical properties of the sample tissue to pH.

By "tissue", as used herein, is meant any tissue or organ present, e.g., in a patient. This definition encompasses any collection of cells, e.g., epithelial cells, muscle cells, skin cells, or any specific organ, e.g., the heart, kidney, or liver, in the patient.

The optical radiation is preferably infrared radiation. Most preferably, the radiation is between 700 and 1100 nm. These wavelengths undergo minimal interference from water absorption in the skin and other tissue, thereby maximizing the penetration depth of the radiation.

The mathematical model is determined prior to the irradiating step by collecting multiple optical spectra, each occurring at known pH values, from a representative sample. The optical spectra and known pH values are then processed with a mathematical multivariate calibration algorithm, such as a partial least-squares (PLS) fitting algorithm described below, to determine the model. This model features a linear or non-linear mathematical equation relating pH to a reflection or absorption spectrum taken from the sample.

Preferably, the processing step includes comparing the optical spectrum to the mathematical model relating optical spectra to specific pH values to determine the pH of the sample tissue.

The representative sample used to determine the model can be the same tissue of the patient which is measured with the optical method. Alternatively, the representative sample is a solution, e.g. in vitro, or second tissue, e.g. an animal tissue, exhibiting optical spectra which vary with pH in a manner similar to a patient's tissue. In all cases, the known pH values are determined using conventional means, such as pH-measuring electrodes.

Once determined, the model is stored, e.g., in the memory of a computer, and then used to transform the optical spectrum measured from a patient into a pH value for a sample tissue. Most preferably, the model used in the analysis step is determined once and is applicable to a wide variety of patients. In this case, the model is preferably robust enough to account for features such as skin color, fat content, weight, etc., which vary from one patient to the next. Alternatively, a range of models can be generated. In this case, during a procedure, the appropriate model is selected and used with a particular patient to determine the pH of a tissue.

The method of the invention can be carried out using a pH-measuring device which includes an array of light sources for delivering radiation to the sample. Preferably, the device includes between 2 and 20 light sources, each of which delivers radiation at a unique range of optical wavelengths. Preferably, each light source is a light emitting diode (LED) or a laser diode. The device also includes a power supply and a modulation system in electrical contact with each of the light sources. The modulation system is configured to modulate electrical power delivered from the power supply to each of the light sources. A detection system included in the device features a first optical detector configured to receive radiation emitted from each light source and then reflected from the sample.

After receiving the reflected radiation, the first optical detector generates a first set of radiation-induced electrical signals, each corresponding to radiation emitted from a separate light source. A signal processor receives the first set of electrical signals and, in response, generates a first set of digital, electrical signals. These signals are then received by a microprocessor. The microprocessor is programmed to process the signals to determine a first spectrum. The first spectrum (or a spectrum determined from the first spectrum) is then compared to a mathematical model to determine the sample's pH. The microprocessor can be additionally programmed to calculate the mathematical model prior to processing the first set of digital, electrical signals.

In preferred embodiments, the modulation system includes electrical power-modulating means (such as a device for modulating the frequency of the power) which modulates the electrical power delivered to each light source at a unique frequency. For example, the power-modulating means can be a conventional circuit that mixes electrical power from a battery with an oscillating waveform. In this case, the detection system further includes phase-sensitive detection electronics in electrical contact with the first optical detector to detect radiation generated at the unique frequency. Preferably, the phase-sensitive detection electronics are incorporated in a lock-in amplifier. In other embodiments, the electrical power-modulating means is configured to deliver electrical power to each light source at a unique time interval. Here, the detection system further includes electronics for gating the first optical detector to detect radiation generated at the unique time interval.

In another embodiment, the device further includes a lens configured to focus radiation from the light sources into a fiber optic cable. The fiber optic cable preferably contains a delivery fiber for delivering radiation to the sample, and a signal fiber for delivering radiation reflected by the sample to the first optical detector.

The optical wavelengths emitted by the light sources are preferably infrared wavelengths, e.g., between 700 and 1100 nm. Preferably, each light source delivers infrared radiation having a bandwidth of between about 10 and 100 nm.

The detection system of the device can also include a second optical detector configured to detect radiation directly from each of the light sources. This radiation can be processed and used to determine a reference spectrum which, in turn, is used to calculate the reflection spectrum. Inclusion of the reference spectrum allows variations in the intensities of each light source to be taken into account. In this case, the device can also include a reference fiber (preferably contained in the fiber optic cable) for delivering radiation from the light sources to the second optical detector.

The invention has many advantages. In general, the pH-measuring device allows facile measurement of pH without contacting the tissue being measured. Measurements made during surgery thus have minimal effect on the procedure at hand. pH measurements can also be made non-invasively by measuring the reflection spectrum of the tissue through the patient's skin. pH of an internal tissue can thus be determined without surgery. In both cases, the non-contact measuring technique is desirable as it can be made safely and without the risk of infection. Measurements can also be made rapidly, and can thus be used during surgical procedures to give the physician immediate feedback on the patient's condition. Measurements are made with high accuracy and are devoid of time-dependent drift sometimes associated with more conventional pH-measuring devices, such as electrodes. In addition, the pH-measuring device of the invention can be either hand-held or used with an endoscopic device. In both cases, the device is easily manipulated and can thus be used to measure pH in hard-to-reach places.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein, including software User's Manuals, are incorporated herein by reference in their entirety. In case of conflict, the present application, including definitions, will control. In addition, the materials, methods, and examples are illustrative only and not intended to be limiting.

Other advantages will be apparent from the following detailed description, and from the claims.

BRIEF DESCRIPTION OF THE DRAWINGS

FIG. 3 is a schematic view showing a pH-measuring device according to the invention;

FIG. 4 is a cross-sectional view of the delivery and signal cables used in the pH-measuring device of FIG. 3 along section line 4—4;

FIG. 14 is a Table showing the results of the mathematical models derived from the reflection spectra taken in FIGS. 11–13;

DETAILED DESCRIPTION pH-Measuring Method

The method according to the invention determines the pH of a sample by measuring and then processing optical data with a series of computational steps. Preferably, the sample is a tissue of a patient, and the optical data is a wavelength-dependent (or frequency-dependent) optical reflection or absorption spectrum. A mathematical model relating actual pH to predicted pH is determined prior to measuring the optical data. The model can be generated, for example, by taking a series of reflection spectra from a number of samples at known pH values, and then processing the spectra and the pH values with a PLS fitting algorithm. Once a model is determined, pH is determined by measuring a reflection spectrum from the sample, and then comparing the spectrum to the model.

Figure 1:
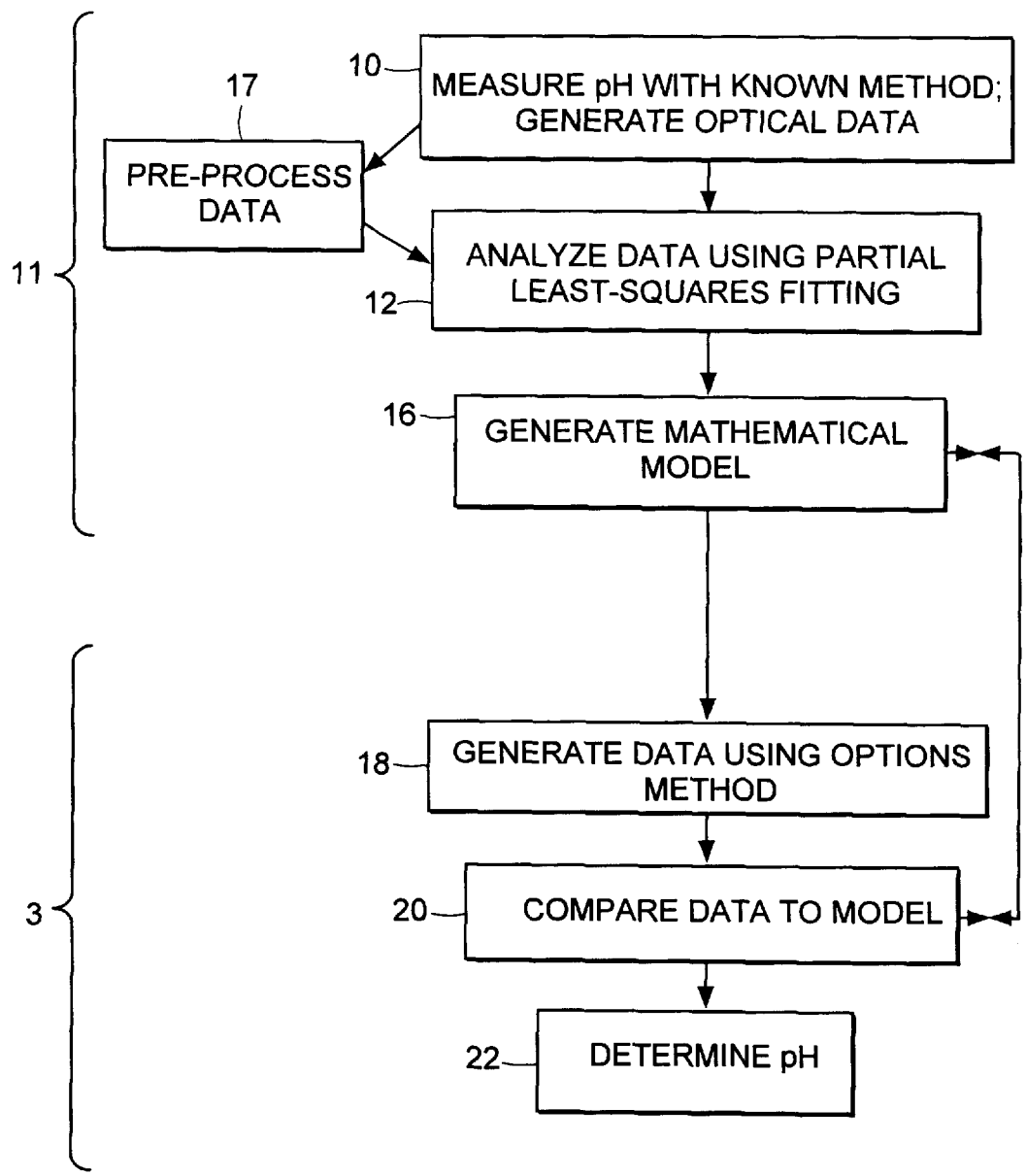
FIG. 1 is a flow chart showing the steps used for pH measurement according to the method of the invention.

FIG. 1 shows a flow chart listing the processing steps used to determine the pH of a sample. The model is first generated with a series of steps (indicated by the bracket 11) and then stored, e.g., in a computer memory. The model is then accessed later in time and used in combination with a second series of steps (indicated by the bracket 13) to determine the sample's pH.

To determine the model, optical data are generated from the sample as the pH is varied. The pH, in turn, is concurrently measured with a known reference sensor, e.g., with an electrode, tonometer, or nmr sensor (step 10). The pH can be varied using any known technique, such as by adjusting the blood flow to a patient's tissue. In this method, variation of the degree of oxygenation causes the pH of the tissue to vary. Because the pH of the sample may exhibit a spatial dependence, optical measurements are preferably taken from an area of the tissue in close proximity to the reference sensor. Reference spectra can be measured to normalize the optical measurements. Both actual pH measurements and optical measurements can be recorded from multiple areas. This allows these values to be averaged together to increase the accuracy of the pH determination.

The actual pH of the sample is recorded as a single numerical value, while the reflection spectrum is in the form of an x-y array of points. The x values of the array represent particular optical wavelengths or frequencies, while the y values represent reflectance intensities corresponding to these wavelengths or frequencies. An absorption spectrum can be determined from the reflection spectrum. In this case, a reference spectrum is taken by placing a highly reflecting reference material on the sample and then measuring the reflected light. The absorption spectrum ($A(\omega)$) can be calculated by taking the log of the reference spectrum ($I_b(\omega)$) divided by the reflection spectrum ($I_r(\omega)$), i.e., $A(\omega) = \log[I_b(\omega)/I_r(\omega)]$.

Spectra for the model can be taken from tissue lying underneath a patient's skin or other tissue, or from the tissue directly. In both cases, infrared optical wavelengths are preferably used to measure the spectra. These wavelengths are particularly advantageous in the former case as they undergo minimal attenuation when passed through skin or covering tissue.

It may be desirable to pre-process the data (step 17) prior to processing with the numerical algorithm (step 12). For example, data containing large amounts of noise can be filtered using well-known smoothing algorithms to improve their signal-to-noise ratio. A particular smoothing algorithm is indicated by equation 1, below:

$$y_{i,ave} = \frac{1}{(n+1)} \sum_{j=i-n/2}^{j=i+n/2} y_j \qquad (1)$$

where i is an integer value indicating a single data point (containing x and y values) in an x-y array. The intensity of the data point (i.e., $y_j$) is averaged together with the intensities of a well-defined set of neighboring data points ranging, for example, from $Y_{i-n/2}$ to $Y_{i+n/2}$, where n is an integer multiple of 2. The averaged intensity value ($Y_{i,ave}$) is then recorded for the frequency or wavelength (i.e., $x_j$) corresponding to the intensity of the data point. This process is repeated for each data point in the x-y array. The degree to which noise and other features in the data are smoothed is increased as the number of neighboring data points (i.e., n) in the well-defined set is increased.

Any of a number of smoothing routines known in the art, such as the Savitsky-Golay algorithm, can also be used to increase the signal-to-noise ratio of the data. This and other conventional smoothing routines are described in "Numerical Recipes Example Book (C), second edition", (William T. Vetterling, eds., Cambridge University Press (1992)).

In other embodiments, the signal-to-noise ratio of the data can be increased by averaging multiple sets of reflection spectra taken for a single pH value. A conventional averaging algorithm is indicated by equation 2, below:

$$y_{i,ave} = \frac{1}{n_{ave}} \sum_{k=1}^{k=n_{ave}} y_{ik} \qquad (2)$$

where $n_{ave}$ is the number of x-y arrays averaged together. k and i are integer counting variables indicating, respectively, a particular x-y array and a particular data point within the array. Thus, $Y_{i=2,k=1}$ is the intensity of the second data point in the first x-y array. Averaging in this way improves the signal-to-noise ratio of the data by $(n_{ave})^{1/2}$. Thus, averaging together ten spectra improves the signal-to-noise ratio over a single spectrum by more than a factor of 3.

Mean-centering is another technique which can be used to pre-process the data prior to processing with the numerical algorithm. In this case, x-y arrays corresponding to different pH values are averaged together as indicated by equation 2 to generate an average x-y array; the average x-y array is then subtracted from each individual x-y array taken at different pH values:

$$\hat{y}_{ik} = y_{ik} - y_{i,ave} \qquad (3)$$

In equation 3, the "hat" over $y_{ik}$ indicates the data point is normalized by the mean-centering operation. Other pre-processing routines include taking a first or second derivative of the spectra prior to processing, or making multiplicative scatter corrections to the spectra (see, e.g., H. Martens and T. Naes, "Multivariable Calibration", J. Wiley & Sons (1989)).

Following pre-processing, a PLS algorithm is used to process the x-y arrays and corresponding pH values (step 12) to generate a mathematical model. PLS algorithms are well-known for statistical analysis of x-y arrays of data points. Other linear regression algorithms, such as least-squares fitting and principal components regression, can also be used to generate the model. These algorithms are described in Thomas, "A Primer to Multivariate Calibration", Analytical Chemistry 66: 795–804 (1994). Preferably, a computer using a commercially available software package incorporating the PLS algorithm is used to process the input data. In preferred embodiments, the Grams/386 software package (Galactic Industries, Inc.) is used to perform the PLS analysis. Alternatively, a similar PLS algorithm can be coded directly into the computer. Such an algorithm is defined, for example, in "Numerical Recipes Example Book (C)", supra. The salient features of the algorithm are described below. A complete guide to the operation of the Grams/386 software is described in detail in the user's manual corresponding to the software package.

The PLS fitting algorithm performs a statistical analysis on the input x-y arrays and known pH values to determine a model relating reflection spectra to the sample's pH. The algorithm is based on a statistical regressive analysis of the relationship between the reflection spectra in the form of the x-y arrays of data points and the pH of the sample. This relationship is described by the following equation:

$$pH_i = \sum_{m=1}^{M} (A_{im} \cdot R_{im}) \qquad (4)$$

where $pH_i$ is the pH of sample i, m is an index for the wavelengths measured in the x-y array, M is the total number of data points in the array, $R_{im}$ is the spectral reflectance (in units of log(1/reflectance)) for sample i at wavelength k, and $A_{im}$ are the PLS regression coefficients calculated by the PLS algorithm. Equation 4 is based on Beers Law, a linear relationship relating the measured absorbance of a sample to its concentration, absorption length, and extinction coefficient. Based on this equation, the PLS algorithm generates a mathematical model (step 16) similar to equation 4 above, wherein the regression coefficients are optimized to best fit the input data. The algorithm also generates other statistical information, described below, indicating the quality and accuracy of the model.

In a qualitative sense, the PLS algorithm determines small pH-induced changes in the reflection spectra and correlates these to the pH value. For example, chemical species, e.g., myoglobin, hemoglobin, water, contained in tissue samples have reflection properties which are pH-dependent; as the pH changes, the reflection spectra of the tissue also changes. The PLS algorithm interprets changes in each x-y array induced by pH, and generates a linear mathematical equation relating the reflection spectra to the predicted pH of the tissue.

The numerical model is made as robust as possible. In general, this is accomplished by taking a large number of spectra at different pH values and under different experimental conditions. The spectra and pH values are then processed using the PLS algorithm as described above. Most preferably, the model is sensitive only to pH-induced changes in the reflectivity of the tissue, and is not affected by the presence of skin. Thus, when the tissue is not exposed with a surgical procedure, reflectivity measurements are made at known pH values using infrared wavelengths which are not strongly absorbed by the skin. In this way, scattering processes in the skin, which are not indicative of the underlying tissue's reflectance properties, are not included in the measured spectra. The model thus does not have to account for skin type, e.g., color, thickness, and optical quality, and other properties related to the skin which have a large degree of patient-to-patient variation.

In addition, the model is preferably not sensitive to parameters associated with the optical measurement, such as the distance between the optical measuring device and the sample, or slight changes in the optical power. The effect of these factors is minimized by taking, during step 10, a variety of reflection spectra and corresponding pH measurements using a variety of experimental conditions.

Moreover, the accuracy of the model is increased by taking measurements at a variety of sample temperatures. Measurements taken at known values of pH with patients having different degrees of fat content, skin roughness and color, height, weight, blood type, and other characteristics can be analyzed and included in the model to increase its accuracy.

Preferably, a single, robust model which is invariant to different patients is determined prior to the optical pH measurement. Alternatively, a range of different models can be determined and stored in the memory of a computer for later use. In this case, the appropriate model is selected according to the patient and used with optical spectra measured from the patient to determine pH. Different models, for example, can correspond to patients having different temperatures, skin color, fat content, etc. As a particular example, temperature can be independently determined by a temperature sensor, e.g., a thermocouple or optical pyrometer, and then analyzed to select different models that are effective for different temperature ranges.

In addition, reflection spectra and pH measurements for the model can be taken from in vitro solutions composed of chemical species typically found in tissue, e.g., water, myoglobin, hemoglobin. Such solutions have the advantage that their properties can be easily changed in a controlled manner, thereby allowing a large number of measurements to be taken under slightly different conditions.

In other alternate embodiments, a model based on only a few spectra and pH measurements is determined for a particular patient undergoing a medical procedure. The conventional pH sensor used to record pH can then be removed. The optical pH-measuring device is used on the same patient along with the model during the remainder of the procedure to determine pH.

The accuracy of the model can be further increased using statistical methods, such as cross-validation. In general, cross-validation is an algorithm used in combination with PLS to obtain an objective assessment of the magnitude of prediction errors resulting from the model. This prediction is made by comparing the x-y arrays or outlier pH measurements (defined below) and pH values input into the model with those which were previously measured and not used in calculating the model. The cross-validation algorithm is included in the Grams/386 software package.

The software package also singles out "outlier" x-y arrays which can decrease the accuracy of the model. Outlier arrays are erroneous data due to non-standard measurement conditions, such as the presence of fingerprints on the sample holder or a large drop in optical power. These data typically have dramatically different properties compared to data measured under more conventional measurement conditions, and thus decrease the accuracy of the pH determination if included in the model. Similarly, outlier pH measurements due to experimental deviations in the reference pH measurements should not be used to calculate the model.

Optical data are taken from the sample (step 18) using the optical pH-measuring device described below to determine the pH once the model is established and stored in a computer memory. Preferably, the device is the same as that used to measure data for the model. As described above, data are in the form of an x-y array of points, where y typically indicates the intensity of the optical measurement, e.g., the reflectivity, as a function of the frequency or wavelength. Measurements from the sample are then multiplied with the PLS regression coefficients of the model (step 20) as indicated by equation 4 to determine the pH (step 22). Alternatively, the data are multiplied by the PLS regression coefficients of the previously determined model to determine the pH.

Figure 2:
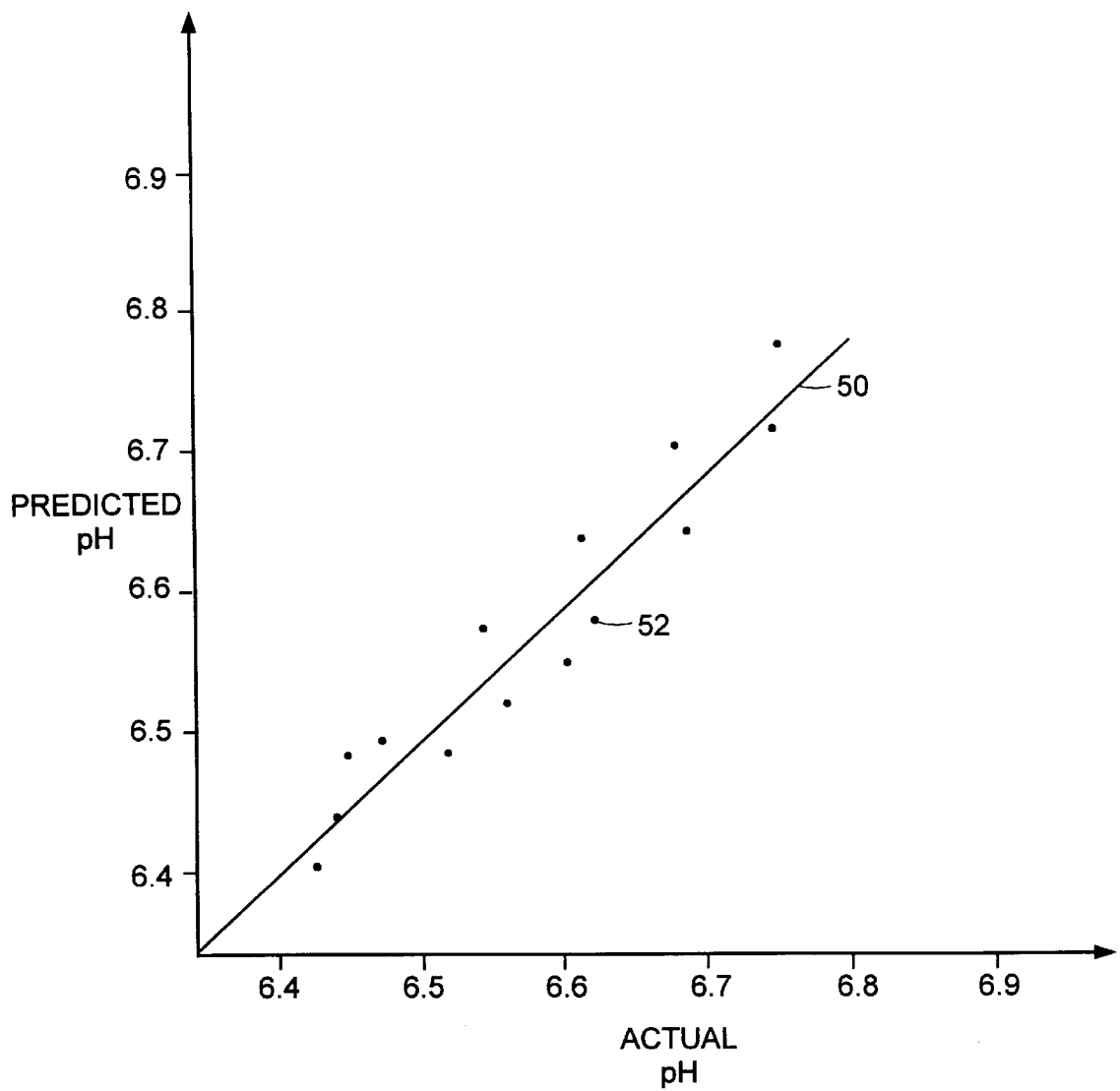
FIG. 2 is a plot of predicted pH as a function of actual pH representative of data generated by the pH-measuring system of the invention.

FIG. 2 shows a representative graph plotting the predicted pH as determined by the model as a function of the actual pH. The line 50 indicates the cases where the pH values predicted by the model are identical to the actual pH. The data points 52 on either side of the line indicate individual pH measurements made with the optical pH-measuring device and processed according to the invention.

The graph is a visual means for determining the accuracy of the model; the separation of the data points from the solid line is decreased as the accuracy of the model is increased. This accuracy can be mathematically represented by the root mean squared difference (RMSD) of the model. This quantity is defined as a measure of the average difference between the actual pH and the value predicted by the model. Most preferably, the RMSD is as small as possible; acceptable models typically have RMSD values less than 0.05 pH units. An R Squared Correlation Coefficient ($R^2$) is a probability value also used to mathematically indicate the accuracy of the model. If the predicted pH is identical to the actual pH, the probability value of the model is perfect. In this case, $R^2=1$, i.e., all points fit the model exactly. Most preferably, the model has an $R^2$ of greater than 0.96. $R^2$ and RMSD are defined mathematically in equations 5 and 6, below:

$$R^2 = \frac{\sum_{i=1}^{n}(Yp_i - \hat{Yk})^2}{\sum_{i=1}^{n}(Yk_i - \hat{Yk})^2} \quad (5)$$

$$RMSD = \sqrt{\frac{\sum_{i=1}^{n}(Yk_i - Yp_i)^2}{n}} \quad (6)$$

where Yk is the measured pH, Yp is the predicted pH, n is the number of spectra, and the "hat" indicates an average value for the measured pH.

pH-Measuring Devices

FIG. 3 shows an optical pH-measuring device 70 for determining the pH of a sample 71. The device 70 features an optical component 72 for generating radiation 74 for measuring the sample's optical properties. The radiation is generated by a radiation source 76, which is preferably a broad-band source, such as an arc lamp. Alternatively, the radiation source is a laser, LED, or any other device capable of generating optical radiation over a range of wavelengths.

Preferably, radiation is emitted in the infrared spectral region. Most preferably, the radiation has wavelengths from 700 nm–1100 nm, as these wavelengths are not significantly absorbed by skin. The depth of penetration in skin for optical wavelengths in this range is about 7 mm. It is thus possible to propagate an optical beam at this wavelength through the skin and onto the muscle (or other tissue) to determine its reflection spectrum.

Prior to irradiating the sample 71, the radiation 74 passes through an optical modulator 78. The modulator can be any device which modulates the temporal or spatial properties of the radiation to facilitate measurement of the sample's optical properties. For example, the modulator 78 can be a spatial filter or lens system which improves the spatial mode of the radiation. In addition, the modulator can be an optical chopper which modulates the time-domain optical properties of the radiation, or a device to modulate the electric power driving the light source.

The radiation 74 can be additionally modulated with a dispersing optic 79 before irradiating the sample. Alternatively, the dispersing optic is placed after the sample. In this case, the dispersing optic is preferably placed immediately before the detector. The dispersing optic is any device which modulates the optical frequencies of the radiation field to facilitate accurate measuring of the sample's optical properties. The dispersing optic is preferably an optical diffraction grating. This device spatially disperses the frequencies of the radiation. The dispersing optic can be rotated with a mechanically rotating device and used in combination with a spatial filter and small-area detector so that individual frequencies of the reflection spectrum can be measured in a point-by-point fashion. More preferably, the dispersing optic is used in combination with a large-area detector, such as a charge-coupled device (CCD) or photodiode, capable of simultaneously measuring a large bandwidth of frequencies.

The radiation is delivered via an optical delivery cable 80 to a probe 82 positioned in close proximity to the sample 71. The cable 80 is secured in the probe 82 using a cable clamp 83. The probe 82 is preferably a hand-held unit which is easily manipulated by the operator. A lens system 84 is included in the probe for focussing the radiation onto the sample. In addition, a heater 86 can be included to prevent moisture condensation on the lens system 84.

During operation, the radiation passes through the delivery cable 80, through the probe, and onto the sample. Reflected radiation 90 from the sample passes through the lens system 84 and through a signal cable 81 which is joined to the delivery cable 80 at the cable clamp 83. The signal cable 81 delivers the reflected radiation 90 through the probe 82 and into an optical signal analysis system 92 for analysis.

The optical signal analysis system 92 includes an optical detection system 94 for detecting the optical signal, and a computational component 96 for processing the optical signal as described above. The optical detection system 94 includes a detection lens system 97 which images radiation onto a radiation-sensitive optical detector 95, such as a CCD or photodiode. The detector generates an electrical signal in response to the radiation which passes through an electrical connector 98 to the computational component 96. The electrical signal is an analog or digital representation of the x-y array of data points described above. Most preferably, the computational component is a computer programmed to process the electrical signal using the method described above.

In preferred embodiments, the optical component 72 and signal analysis system 92 of the pH measuring device are provided by a commercially available infrared optical spectrometer. Such spectrometers are available, for example, from Ocean Optics, Analytical Spectral Devices, and Near IR Systems.

FIG. 4 shows a cross-sectional view of the probe 82 which includes the optical delivery cable 80 and the signal cable 81. Both cables may contain single strands of optical fibers or fiber optic bundles containing multiple optical fibers. Most preferably, the optical fiber from the delivery cable is disposed near the center of the probe; the optical fibers from the signal cable are preferably disposed radially from the center. One or more additional signal cables can be included in the probe to increase the amount of radiation delivered to the signal analysis system. Typically, the optical delivery and signal fibers have, respectively, diameters of between about 0.5 and 2 mm and 50 to 500 microns.

Figure 5:
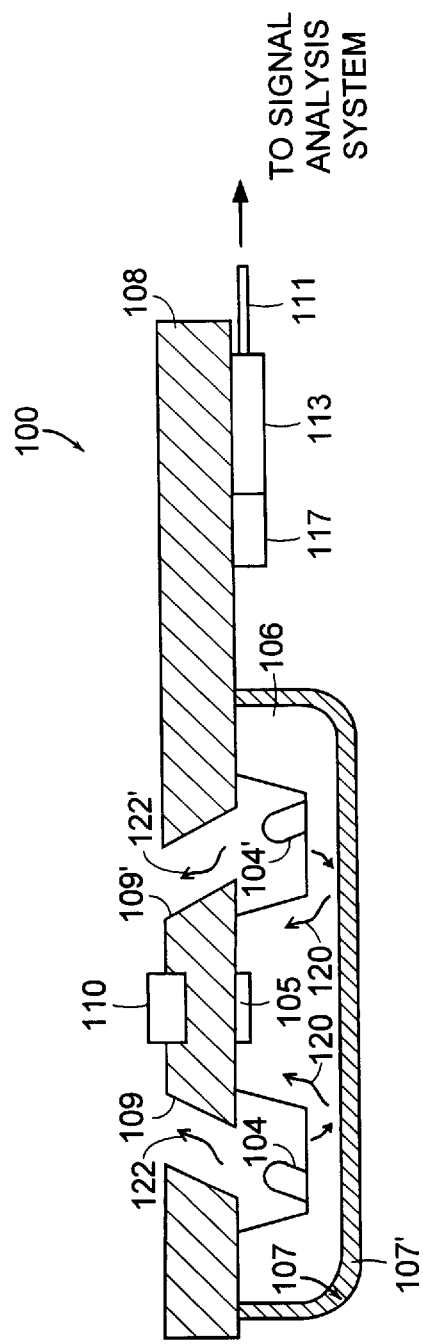
FIG. 5 is a cross-sectional view of an integrated pH-measuring device according to the invention.
Figure 6:
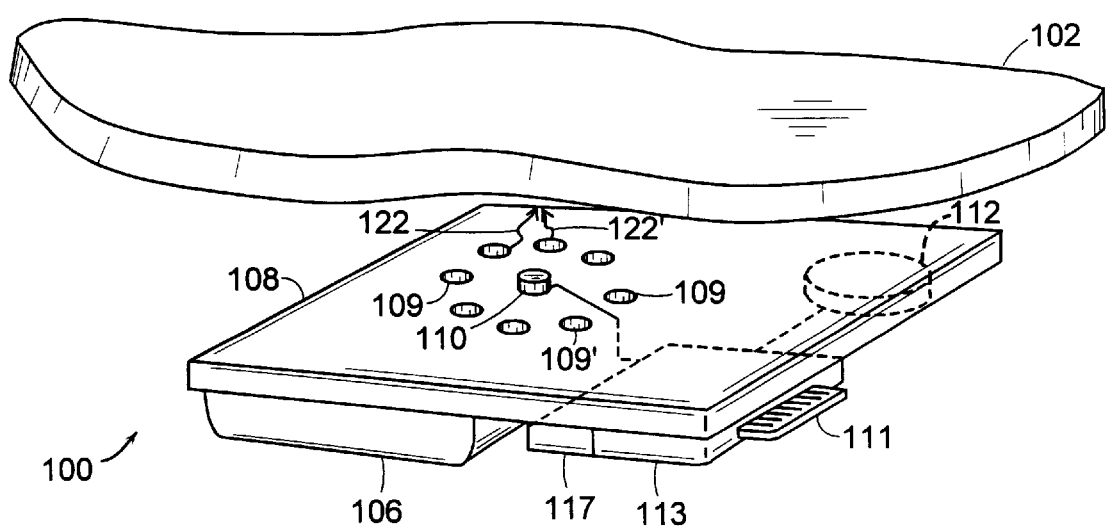
FIG. 6 is a perspective view showing the integrated pH-measuring device of FIG. 5 measuring a sample.

FIGS. 5 and 6 show an integrated, self-contained pH-measuring device 100 for measuring a reflection spectrum from a sample 102. The pH-measuring device 100 features an array of light-emitting diode (LED) radiation sources 104, 104' for providing optical radiation. Each LED in the array emits radiation having a different central infrared wavelength. The bandwidth of radiation from each LED is typically between about 10 and 100 nm. In this way, the collective radiation from the array is effectively equivalent to a broad-band infrared optical source. Most preferably, the LEDs collectively emit radiation in the range of 700–1100 nm. Reflection spectra taken in this range can then be processed with the above method to determine the sample's pH.

The LEDS are mounted inside a metallized reflective cover 106. The cover 106 is preferably composed of an optically transparent material, such as glass or plastic, which is coated on its inner surface 107 with a reflective material 107'. For example, the reflective material can be a metal or dielectric optical coating.

The cover 106 is attached to a mounting plate 108. The mounting plate 108 includes a series of portholes 109, 109' positioned above each LED so that radiation 122, 122' can pass through the mounting plate 108 and onto the sample. Preferably, the pH-measuring device includes between 2 and 20 LEDs; a single porthole is preferably included for each LED. The LEDs are preferably tilted inward so that radiation leaves the device at an angle relative to the mounting plate. In this way, each LED can irradiate approximately the same part of the tissue, thereby increasing the accuracy of the measurement. Alternatively, the LEDs can be leveled so that radiation is emitted upwards in a vertical direction. In both cases, the LEDs and portholes are preferably evenly spaced and arranged in a circular pattern on, respectively, the cover 106 and mounting plate 108.

The device 100 includes interior 105 and exterior 110 detectors for detecting radiation. Most preferably, both the interior and exterior detectors include photodiodes and detection electronics, such as electrical circuits for gated or phase-sensitive detection, for generating analog electrical signals in response to infrared optical frequencies. The exterior detector 110 is attached to the outer surface of the mounting plate. During operation, optical radiation 122, 122' from each LED is emitted in all directions. A majority of the radiation 122, 122' passes through the portholes 109, 109' and onto the sample 102. This radiation is partially reflected by the sample towards the exterior detector 110 for detection.

The interior detector 105 is attached to the bottom surface of the mounting plate 108. As the sample is irradiated, a portion 120 of the radiation emitted by the LED propagates to the reflective cover 106 and is reflected by the reflective material 107' towards the interior detector 105. In this way, the interior detector 105 monitors the optical output emitted from the LEDs. Alternatively, the air space between the reflective cover and the mounting plate which surrounds the LEDs can be filled with an optically transparent polymer encapsulant. This material increases the device's resistance to mechanical shock and vibrations. Radiation detected by the interior detector is used to determine a reference spectrum which allows intensity variations from the various LEDs to be accounted for. The actual reflectivity spectrum is calculated by taking the ratio of the reflected radiation, as measured with the exterior detector, to the reference spectrum, as measured with the interior detector.

A signal processor 113, power supply 112, and modulation system 117 are connected directly to the mounting plate 108. The power supply 112 supplies electrical power to the LED radiation sources and the interior and exterior detectors. Prior to being supplied to the LEDs, electrical power passes first through the modulation system 117. The modulation system 117 then pulses the electrical power so that each LED receives power and emits radiation during a separate time period. The time periods are temporally offset so that individual LEDs in the array emit radiation in a time-dependent, sequential manner. Radiation reflected from the sample will thus arrive at the exterior detector during separate time periods corresponding to those when the LEDs are powered. In this embodiment, the exterior detector is gated so that radiation arriving at the separate time periods is detected separately. Radiation is detected by the interior diode using similar means.

Alternatively, electrical power supplied to each LED can be modulated at a different frequency by the modulation system. This, in turn, drives each LED to emit radiation at a different modulation frequency. (Note that the modulation frequency is not the optical frequency of the radiation emitted from the LED.) Radiation reflected from the sample has the same frequency as the LED's modulation frequency. In this case, the exterior detector includes phase-sensitive detection electronics, such as a lock-in amplifier, so that the radiation corresponding to each LED can be detected. As before, radiation is detected by the interior detector using similar means.

In both cases, the radiation-induced analog electrical signals generated by the interior and exterior detector are sent to the signal processor 113 for analysis. When the incident radiation is modulated in a sequential, time-dependent fashion, the signal processor separates the individual signals measured by both the gated interior and exterior detectors. When the incident radiation is frequency-modulated, the signal processor separates the signals occurring at different modulation frequencies. The signals are then amplified and digitized with conventional analog-to-digital electronics contained within the signal processor.

Typically, the power supply provides a voltage of between about 2.5 and 3.5 V, and a current of between about 5 and 100 mA. Power can be modulated between about 100 Hz and 10 kHz for frequency modulation, or can be delivered to the LEDS in time intervals ranging from about 100 microseconds to 10 milliseconds for temporal modulation. Standard electrical batteries and circuits known in the art can be used for these purposes. Alternatively, a function generator and signal amplifier can be used to generate the frequency-modulated signal at the appropriate voltage and current.

Once separated, amplified, and digitized, the signals can be sent through an output connector 111 to a computer for processing. The computer pieces together the reflection spectrum from the individual signals generated by the interior and exterior detectors. The final spectrum can then be displayed and analyzed as described above with the computer to determine the sample's pH.

In another embodiment, a separate microprocessor is included directly in the pH-measuring device. The microprocessor receives the radiation-induced signals from the signal processor to calculate the reflection spectrum. The spectrum can then be further analyzed to calculate the pH of the sample using the method described above. This embodiment can be used to determine the pH of the sample without using an external computer, and is thus particularly desirable for applications necessitating a portable or hand held device.

To minimize size and facilitate operation, the LEDs of the integrated pH-measuring device are preferably patterned directly onto a printed circuit board (or other substrate) using standard integrated, hybrid, or printed circuit fabrication techniques. The signal receiving system, power supply, and optical modulation system can be attached to the circuit board using epoxy or equivalent adhesive materials.

Because of its small size, the integrated device is portable, hand-held, and easily manipulated. This allows the operator to measure pH in hard-to-reach places on a particular patient; pH can also be measured in remote locations, such as in an ambulance or outdoors. The integrated device also can be used as a body-worn sensor for continuous monitoring of pH.

Figure 7:
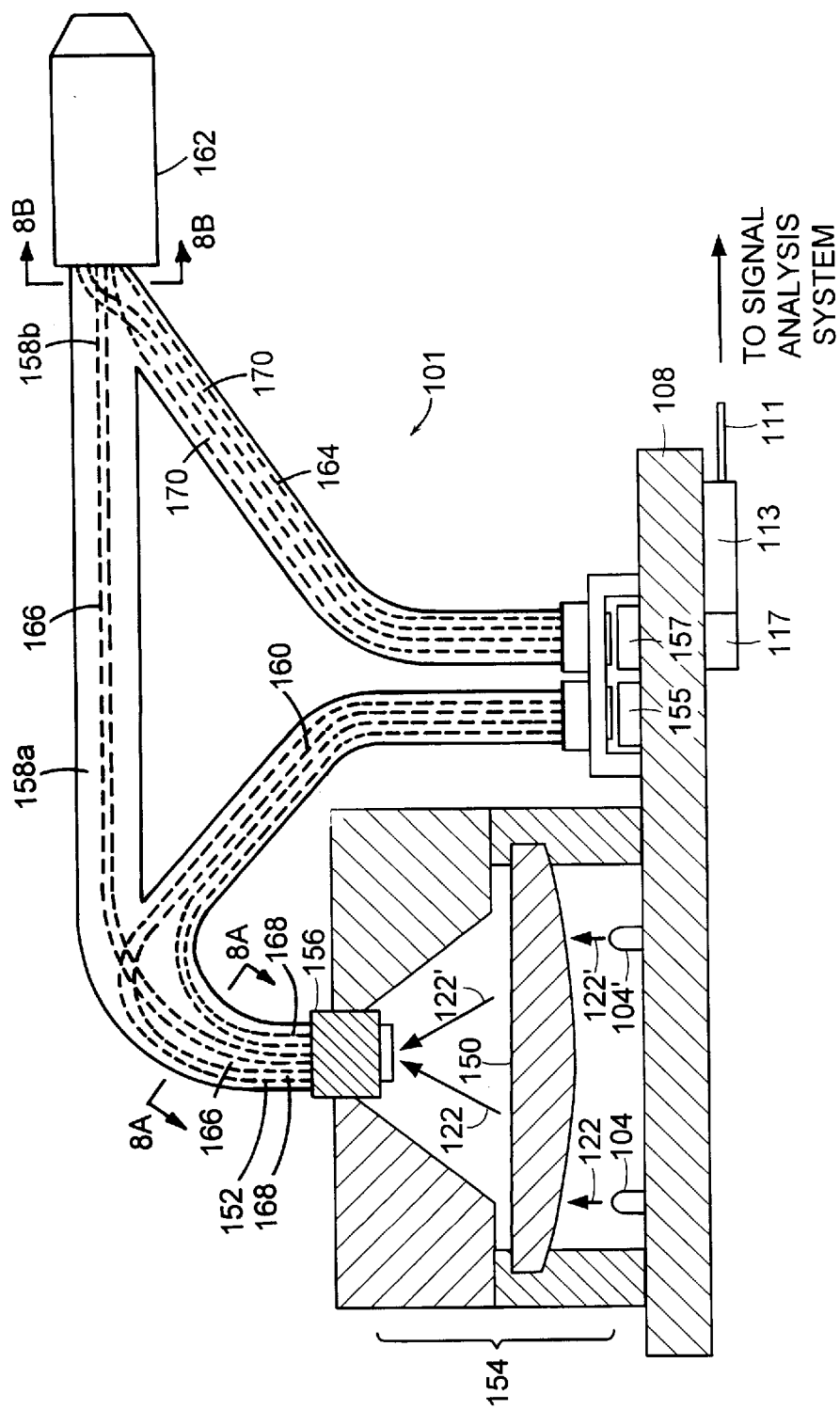
FIG. 7 is a cross-sectional view of an alternate embodiment of the integrated pH-measuring device according to the invention.

FIG. 7 shows another embodiment of an integrated optical device 101 wherein radiation 122, 122' from the LEDs 104, 104' is focussed by a lens 150 and into a fiber optic cable 152. A lens housing 154 attached to the mounting plate 108 is used to support both the lens 150 and an annular fiber housing 156 disposed radially around the fiber optic cable 152. In this embodiment, the LEDS 104, 104' are mounted directly on the mounting plate 108, and the device does not include a reflective cover.

The power supply (not shown in the figure) and modulation system 117 described above are used to modulate radiation from the LEDs as a function of time or frequency. The modulated radiation is then processed with the signal processor 113 as described above so that reference and reflection spectra can be pieced together. Spectra can be processed with a microprocessor in the device to determine the sample's pH. Alternatively, the spectra can be sent through the output connector 111 to a computer for processing.

Figure 8A:
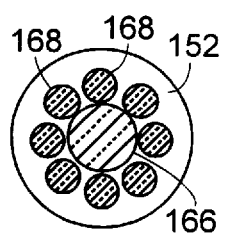
FIGS. 8A and 8B are cross-sectional views of the fiber optic cable of FIG. 7 along, respectively, section lines 8A—8A and 8B—8B.

The fiber optic cable 152 is bifurcated at a first point 158*a* to deliver a portion of the incident radiation through a first fiber optic cable section 160 to a reference detector 155. This radiation is then processed to determine the reference spectrum. Accordingly, as shown in FIG. 8A, a cross-sectional slice of the fiber optic cable 152 immediately after the fiber housing 156 features a delivery fiber 166 surrounded by radially and symmetrically disposed reference fibers 168. During operation, radiation from the LEDs is focussed by the lens into both the delivery 166 and reference fibers 168. Radiation from the delivery fiber passes through the cable and onto a sample, while radiation coupled into the reference fibers propagates through the first fiber optic cable section 160 and onto the reference detector 155.

Figure 8B:
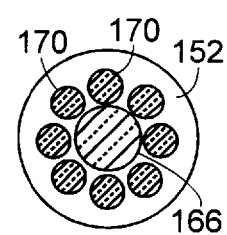

The radiation delivered by the fiber optic cable passes through a probe 162 prior to irradiating the sample. FIG. 8B shows a cross-sectional slice of the fiber optic cable 152 immediately before the probe 162. Here, a series of signal fibers 170 are radially and symmetrically disposed around the delivery fiber 166. In addition, the cable is bifurcated at a second point 158*b*. During operation, radiation reflected by the sample is collected by the signal fibers 170 and delivered through a second cable section 164 to a signal detector 157. This radiation is then processed as described above to determine the reflection spectrum.

Both the reference 168 and signal 170 fibers are preferably disposed around the delivery fiber 166 in a radial, symmetric pattern to maximize the coupling efficiency of, respectively, the incident and reflected radiation. Use of multiple fibers also facilitates optimal collection of radiation.

Figure 9:
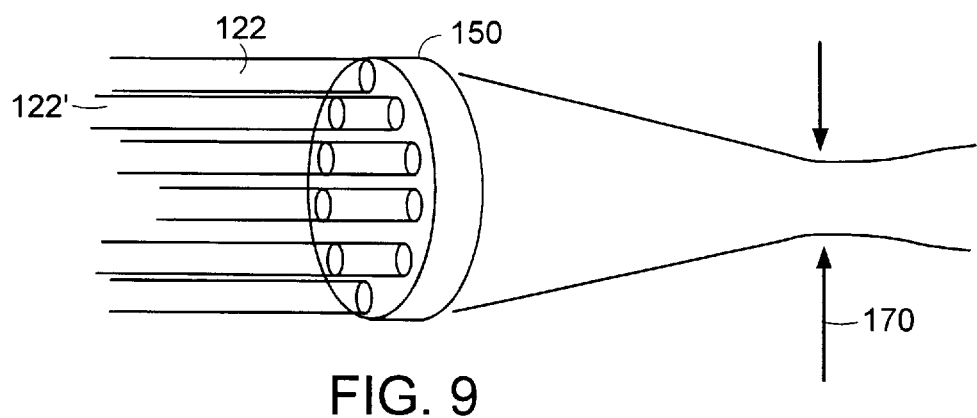
FIG. 9 is a perspective view of a lens in the device shown in FIG. 7 being irradiated by a series of LEDs.

FIG. 9 shows a preferred orientation of the lens 150 of FIG. 7 relative to the incident radiation 122, 122' generated by the LEDs. Preferably, the LEDs are arranged in the integrated optical device so that the incident radiation irradiates the lens in a symmetric, ring-like pattern disposed radially around the center of the lens 150. The lens is preferably placed as close as possible to the LEDs to minimize radiation losses due to beam divergence. In this way, the collective incident radiation from all the LEDS can be focussed to as small a spot (indicated by the arrows 170) as possible, thereby maximizing the amount of radiation coupled into the fiber optic cable.

Method of Use

The pH-measuring device of the invention can be used to determine the pH of muscle and a wide variety of other tissues. Tissue can be measured directly or after propagating the infrared radiation through the skin. In particular embodiments, the device is used during critical care medicine and cardiac, orthopedic, or plastic surgeries to determine the pH of tissue.

For example, during cardiac surgery, the pH-measuring device is used to monitor a region of the heart to ensure proper delivery of cardioplegia, a substance which arrests the heart and additionally provides it with nutrients so that it will effectively beat again once the operation is completed. Non-invasive measurements can be made continuously or intermittently. pH monitoring additionally ensures good blood perfusion through completed vein grafts. This is particularly advantageous for procedures such as transmyocardial revascularization, a procedure which uses laser radiation to create new blood pathways in the heart. In this case, the patient's chest is not open, and thus pH (and the corresponding degree of ischemia) is measured to ensure that the diseased region of the heart is properly revascularized.

The pH-measuring device can also be used in critical-care medicine to measure the pH of a patient's stomach lining or intestines. This allows shock and organ failure to be determined non-invasively. The device of the invention can, for example, replace tonometers, nmr spectrometers, and related devices used to measure pH. Other applications include those in orthopedics and plastic surgery, where pH can be measured non-invasively to determine the degree of ischemia.

In addition, it has been shown that in certain cases, the pH of metabolically active cancer cells is different than that of normal cells. Moreover, metabolism is accelerated in cells undergoing healing after a wound and burn, thus causing the cell's pH to change. Thus, by focussing the radiation field of the pH-measuring device onto a small region of cells, their pH can be estimated to detect cancerous cells and determine the degree of tissue healing.

In addition, pH-measuring devices such as those shown in FIGS. 3 and 7 can be used with minimally invasive surgical devices, such as endoscopes, to measure pH of a tissue. In these cases, radiation is coupled into optical fibers and used to measure reflection spectra. Particular examples of minimally invasive surgical devices include arthroscopes, which are used, e.g., for arthroscopic knee surgery. This device requires only small incisions to be made in the tissue prior to inserting the endoscope. In this way, it is possible to measure pH of internal organs.

Other uses include use of the pH-measuring device to determine the pH of the colon, stomach, intestines, liver, kidneys, and other internal organs.

The following examples are used to further describe the embodiments of the invention.

EXAMPLES

Surgical Procedures and Instrumental Set-Up

Surgery was performed on 7 rabbits (numbered 3J through 9J) pre-anesthetized with a ketamine/xylazine mixture. The abdomen and back of each rabbit was shaved and cleaned. A tracheal tube was inserted and the animal ventilated with approximately 2% isoflurane plus 98% oxygen (tidal volume≈100 ml, rate≈30 breaths/min). The carotid artery was dissected so that a Millar pressure transducer could be placed therein to monitor systemic blood pressure. The femoral artery was exposed and a 20-gauge catheter was placed to facilitate the collection of blood samples for blood gas analysis. The blood gas samples were used to adjust ventilation during the experiment to maintain a proper acid-base balance.

The latissimus dorsi muscle flap and skin covering were first removed to expose the teres major muscle on the animal's right side. The teres major muscle was dissected from the scapula and a single artery feeding the muscle was isolated. A chemical heating pad was placed in contact with the muscle for temperature control. Electrochemical electrode-based pH probes (1.3 mm in diameter) were implanted along the left and right sides of the teres major muscle. An agar bridge connecting the implanted electrodes to the reference electrode was implanted in fat under the rabbit's skin, against the back muscle. A temperature probe was implanted with one of the pH probes. A clamp or inflatable occluder was placed across the artery connecting the teres major muscle to the rest of the rabbit.

Spectrometer

An Ocean Optics spectrophotometer system providing measurements between 500 nm and 1000 nm was used to collect a reflection spectrum for rabbits 3J, 4J, 5J, 6J, and 8J. For rabbits 7J and 9J, a Near IR Systems spectrophotometer operating in both the visible and near infrared (400 nm –2500 nm) was used to collect data. Signal-to-noise ratios were superior with the Near IR Systems spectrophotometer, though this may be related to post-acquisition signal processing (see below). The Near IR System was much more sensitive to room lights.

For the Ocean Optics system, two reference materials (an aluminum plate and a spectral on substrate, a translucent, white material) were used to collect reference spectra. The spectralon provided a more consistent reference and was used with the Ocean Optics System. The aluminum plate was used for the Near IR Systems spectrometer. The plate was placed directly on the muscle to collect the reference spectrum in exactly the same configuration as that used to collect the reflection spectrum of the muscle. The reference and reflection spectra were used to calculate an absorbance spectrum as described above.

Probe Configuration

An aluminum probe mount assembly containing delivery and signal fiber optic cables separated by an angle of approximately 60° was used with the Ocean Optics System on rabbits 3J and 4J. A probe with collinear delivery and signal fiber optic cables (similar to that shown in FIGS. 3 and 4) was used with rabbits 5J, 6J, and 8J. It was possible to position the probe with collinear fiber optic cables closer to the muscle surface, allowing a stronger signal to be collected.

With the Near IR Systems spectrometer, delivery and signal cables separated by angles of 30° and 60° were used to collect reflection spectra for, respectively, rabbit 7J and rabbit 9J. The signal-to-noise ratio was improved for the 60° angular separation.

The optimal height for each probe configuration was determined by measuring the intensity of radiation returned from a reflector placed on the rabbit's skin. The optimal height (determined to be between about 0.1 and 2.0 mm) was that which gave the largest signal without saturating the spectrometer's detector.

Measurement of pH

Once the rabbit was anesthetized as described above, the probe was placed over the muscle and the height adjusted to its optimal position. The reference spectrum was then collected. The clamp or occluder was then closed to produce ischemia in the teres major muscle. pH was recorded every 20 seconds with the 2 micro-electrodes while reflection spectra were collected every 5 minutes. pH and spectral data were collected until the pH stopped decreasing (60–90 min.) at which time the clamp or occluder was released to reperfuse the muscle and increase the pH (except in rabbit 3J, where the clamp was not released).

After monitoring both decreasing and increasing pH on rabbits 4J and 9J, a piece of the rabbit's skin was removed, shaved to remove the fur, and cut to approximately the size of the teres major muscle. The skin was placed hair-side-down on top of the muscle and the probe was returned to the optimal height. The clamp was closed and pH and spectral data were collected until the pH stopped decreasing.

For the pH to drop at a reasonable rate (i.e., 0.02–0.04 pH units per 5-minute period), it was necessary to maintain the muscle temperature above 33° C. This was accomplished by placing the chemical heating pad under or on top of the muscle so that interference with the optical probe was minimized. Condensate on the probe housing and fiber optic cables was avoided by gluing small heating tapes to the probe housing.

Spectra from both the rabbit and the reference material were measured using the Ocean Optics system and then processed with the Grams/386 software to calculate an absorption spectrum. The data were then smoothed with a 21-point Savitsky-Golay smoothing routine. The smoothing removed the high-frequency noise components, but did not remove the low-frequency components that were particularly evident between 900–1000 nm. The Near IR Systems spectrometer collected and averaged 64 spectra, calculated absorbance, and smoothed the result.

The absorbance spectra and the recorded pH values from the micro-electrodes were used with the Partial Least Squares -1 (PLS-1) routine in Grams/386 to derive models for predicting pH from the spectral data. Mean-centering was used to pre-process the data before the PLS-1 routine was run. The PLS-1 routine included cross-validation algorithms for improving the accuracy of the model. After the routine was run, the optimal number of regression factors was selected for the model. The Grams software package provided F-ratios and probability values for each regression factor. The Grams manual indicates that the user select the factor number which has a probability value just under 0.75. In addition, outlier spectra were identified as those samples that have a spectral or concentration residual F-ratio greater than 3 and a probability of being an outlier of greater than 95%. Spectra that were visual outliers and were known to be different from the set, e.g., because of probe motion or water condensation, were also eliminated. All outliers were then eliminated and the model re-run.

To evaluate the success of the experimental setups, $R^2$ and RMSD values for each of the rabbits were reported. Early experiments showed promising results with continually decreasing pH. To ensure the effect was not due to another factor related to time, such as the muscle drying out, the clamp was released and increasing and decreasing pH were incorporated in the same model. Knowing the optimal number of factors, an actual vs. predicted pH plot was produced for each model. The derived model was used to predict the pH from each of the sample spectra used to generate the model.

Figure 10:
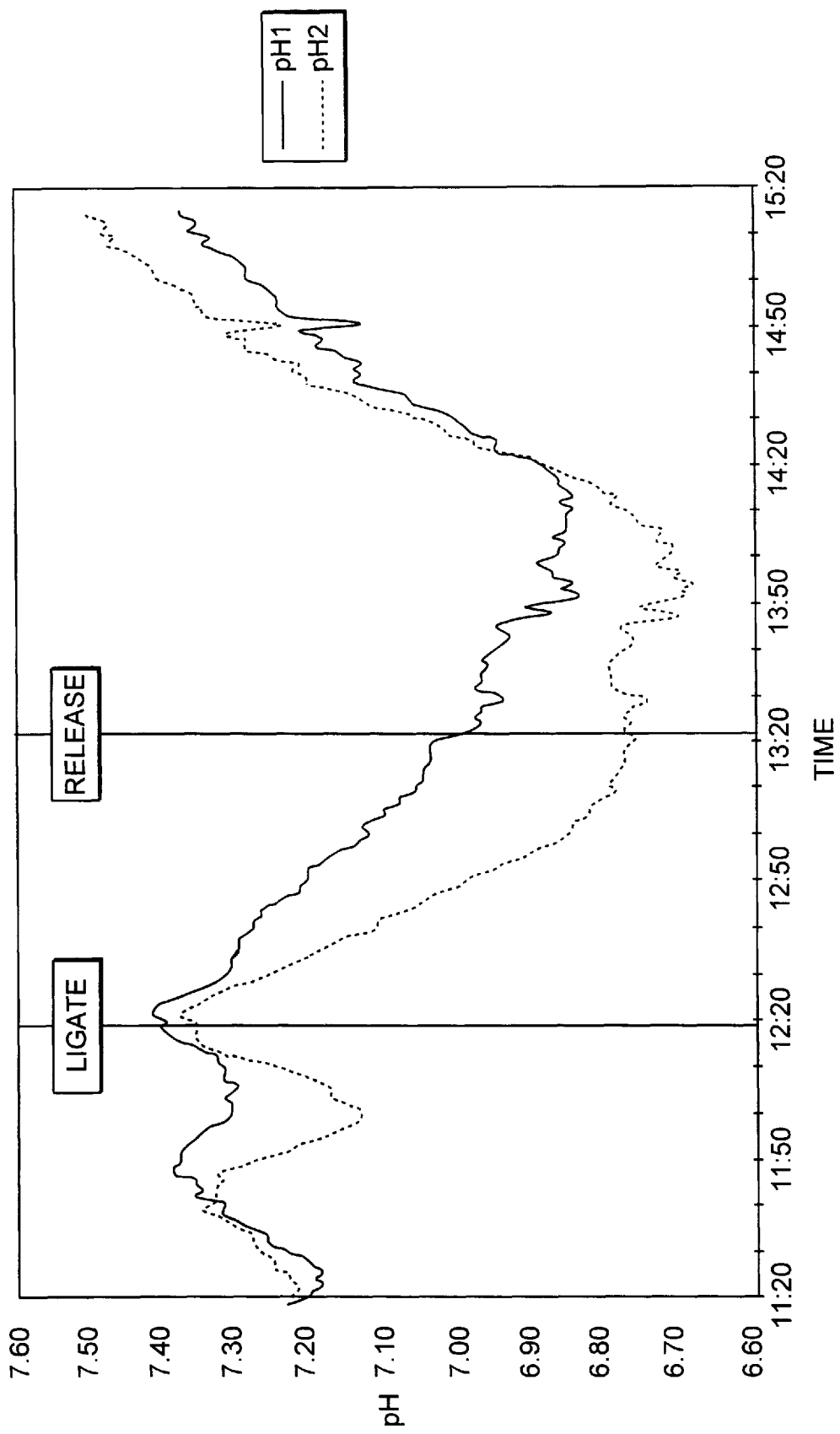
FIG. 10 is a graph of the time-dependent pH of a bare muscle of a live rabbit measured using conventional electrodes.

FIG. 10 shows a graph plotting the time-dependent pH of a rabbit (in this case, rabbit 5J) measured during a typical experiment. The pH was measured using the microelectrodes and no skin covering the rabbit's muscle. At the beginning of the experiment, the tissue pH starts at about 7.26±0.18 pH units. A single pH electrode (pH1) typically reads differently from another (pH2) by 0.2–0.3 pH units. This difference in reading may be due to trauma induced to one of the sites during placement of the electrode or to differences in temperature. During ligation, the pH drops an average of 0.49±0.12 pH units before leveling off. When the ligation is complete, the pH raises an average of 0.60±0.17 pH units to reach levels near the blood pH which is typically alkalotic.

Figure 11:
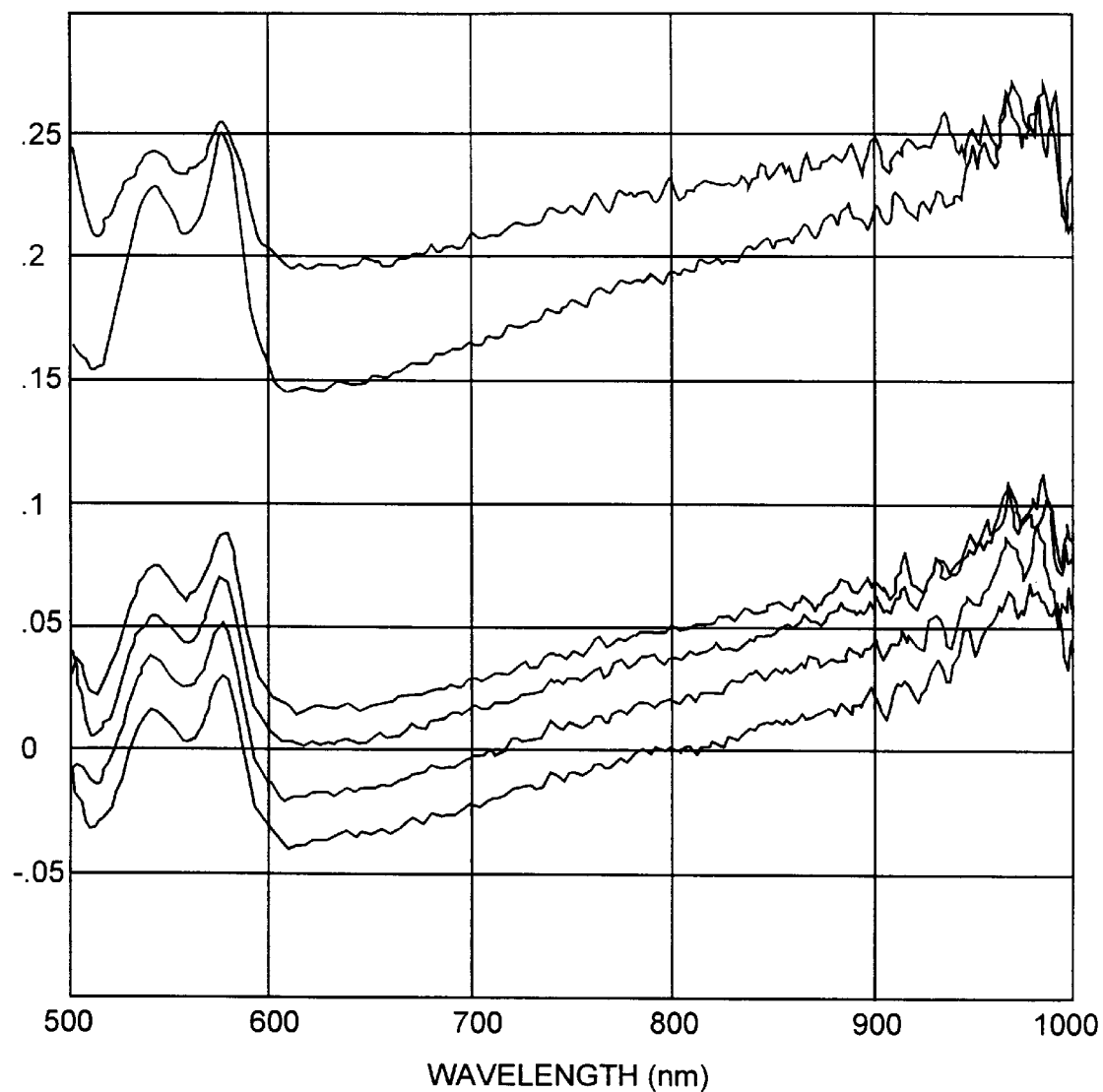
FIG. 11 is a series of reflection spectra collected from bare rabbit muscle as a function of increasing pH.
Figure 12:
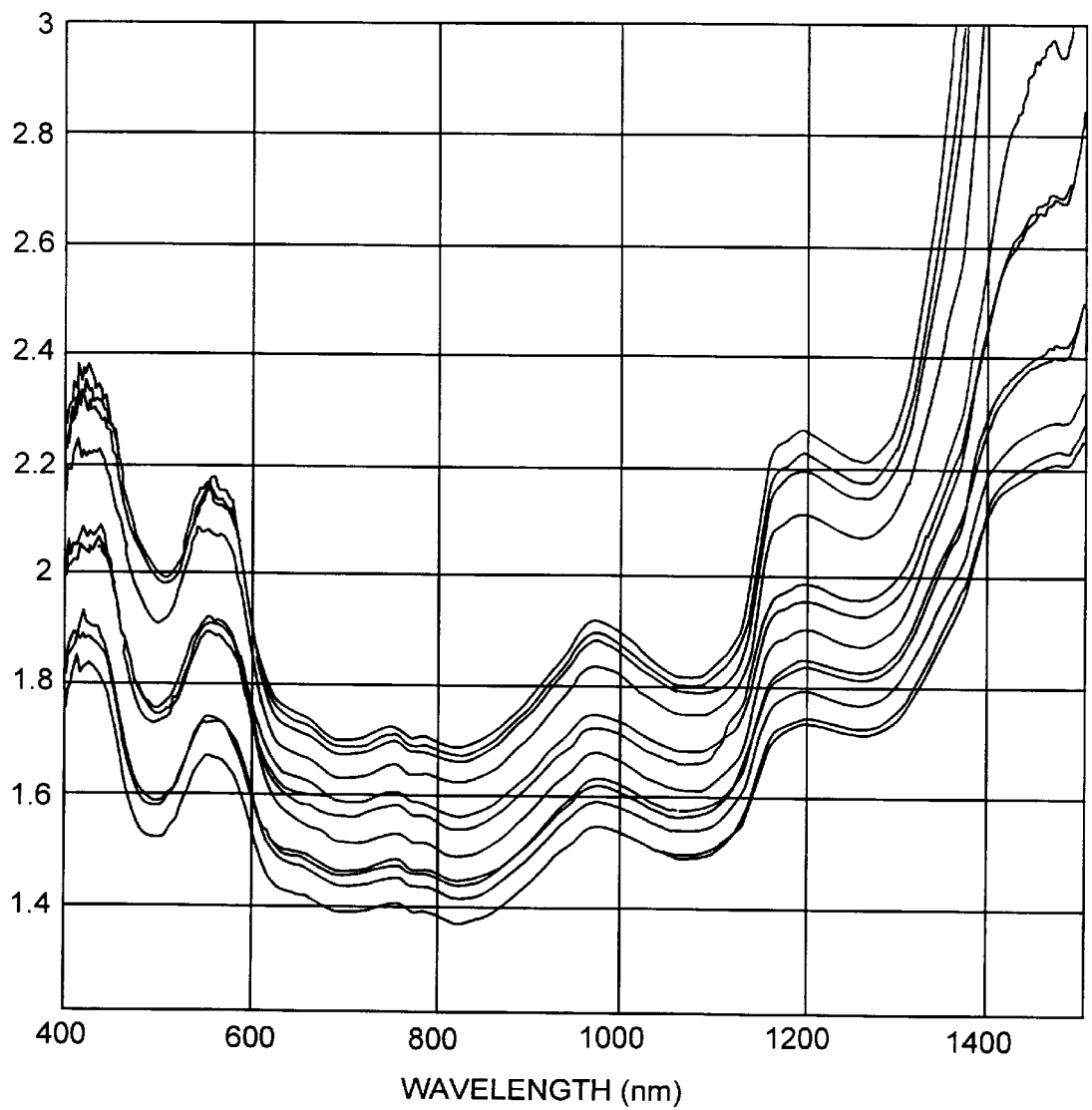
FIG. 12 is a series of reflection spectra collected from bare rabbit muscle as a function of increasing and decreasing pH.
Figure 13:
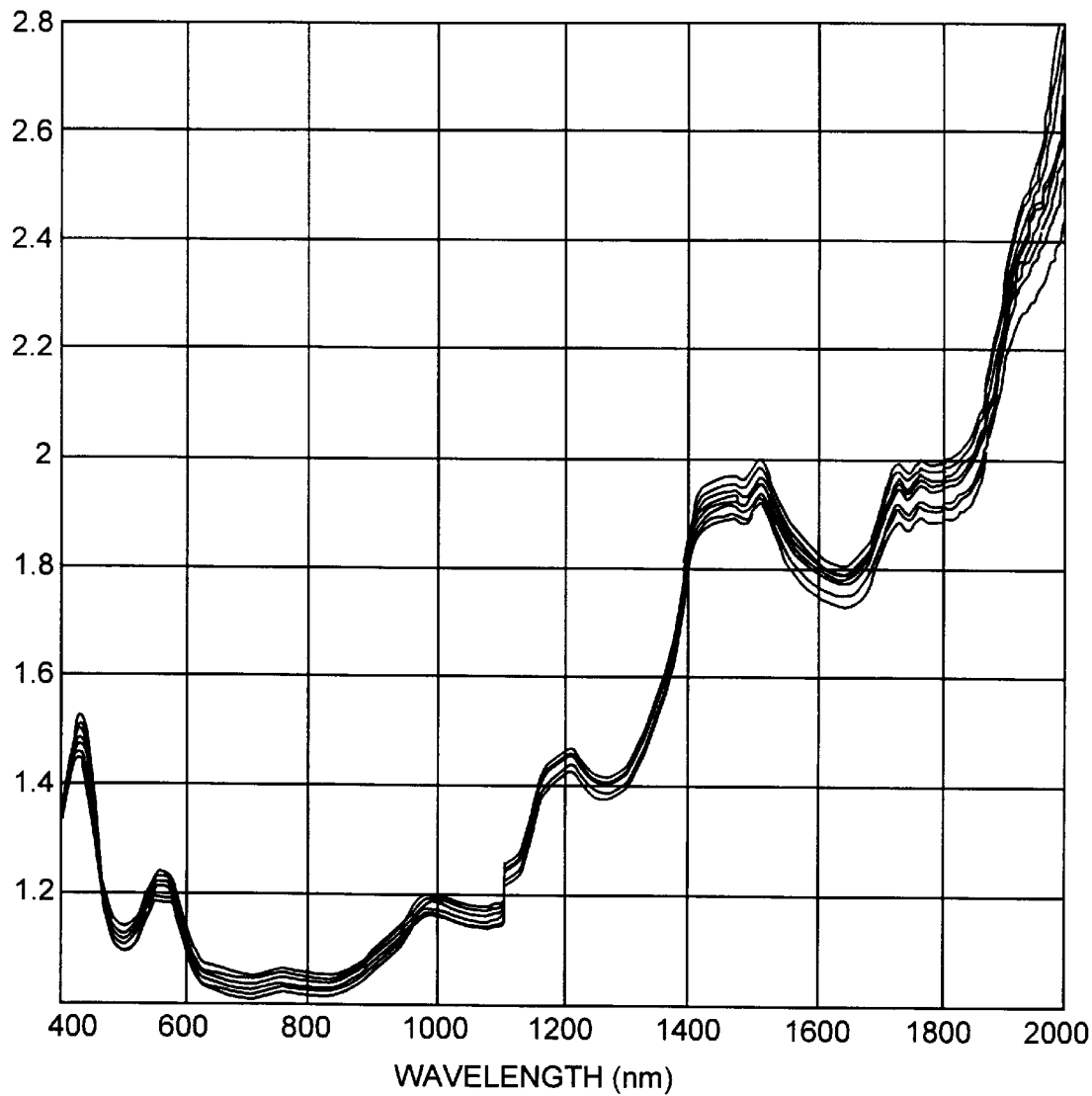
FIG. 13 is a series of reflection spectra collected from skin-covered rabbit muscle as a function of decreasing pH.

Typical spectra collected using the Ocean Optics and Near IR Systems spectrometers are shown in FIGS. 11–13. FIG. 11 shows a plot of various spectra collected using the Ocean Optics spectrophotometer from rabbit 6J as the pH is increased. Data between 500 nm and 1000 nm were collected. A resolved doublet is observed at 542 nm and 577 nm on most of the spectra. There appears to be a peak at 980 nm, although it is difficult to resolve above the noise. FIG. 12 is a plot of selected spectra collected from bare muscle on rabbit 9J using the Near IR Systems spectrophotometer. Spectra are collected as the pH is both lowered and raised. The spectral data are only recorded between 400 nm and 1500 nm because water condensation on the probe obscured data at longer wavelengths. The doublet observed with the Ocean Optics system is not resolved, but peaks at 426, 556, 748, 975, 1196, and 1466 nm are evident.

FIG. 13 is a plot of the spectra of the same muscle covered with a skin flap taken as the pH is lowered. Spectra between 400 nm and 2000 nm were recorded. The spectra are broken into two regions ranging from 400–1100 nm and 1100–2000 nm. Joining of the two regions results in the discontinuity in the plot near 1100 nm. Comparison with FIG. 12 indicates that similar peaks were observed in the covered and bare muscle. Additional peaks in the skin-covered muscle were also recorded at 1510, 1728, 1766 nm.

The spectra shown in FIGS. 11–13 were processed with the Grams/386 software to generate models as described above. FIG. 14 is a Table summarizing the results from rabbits 3J–9J derived using the spectroscopic data and the models. "None" means no models could be fit to the data, while "N/A" means that the particular experiment was not performed. Models were run with approximately 15 points for the uni-directional change in pH and with 30 points when pH was both increased and decreased. Models were run over the entire spectral range covered by the spectrophotometer.

Figure 15:
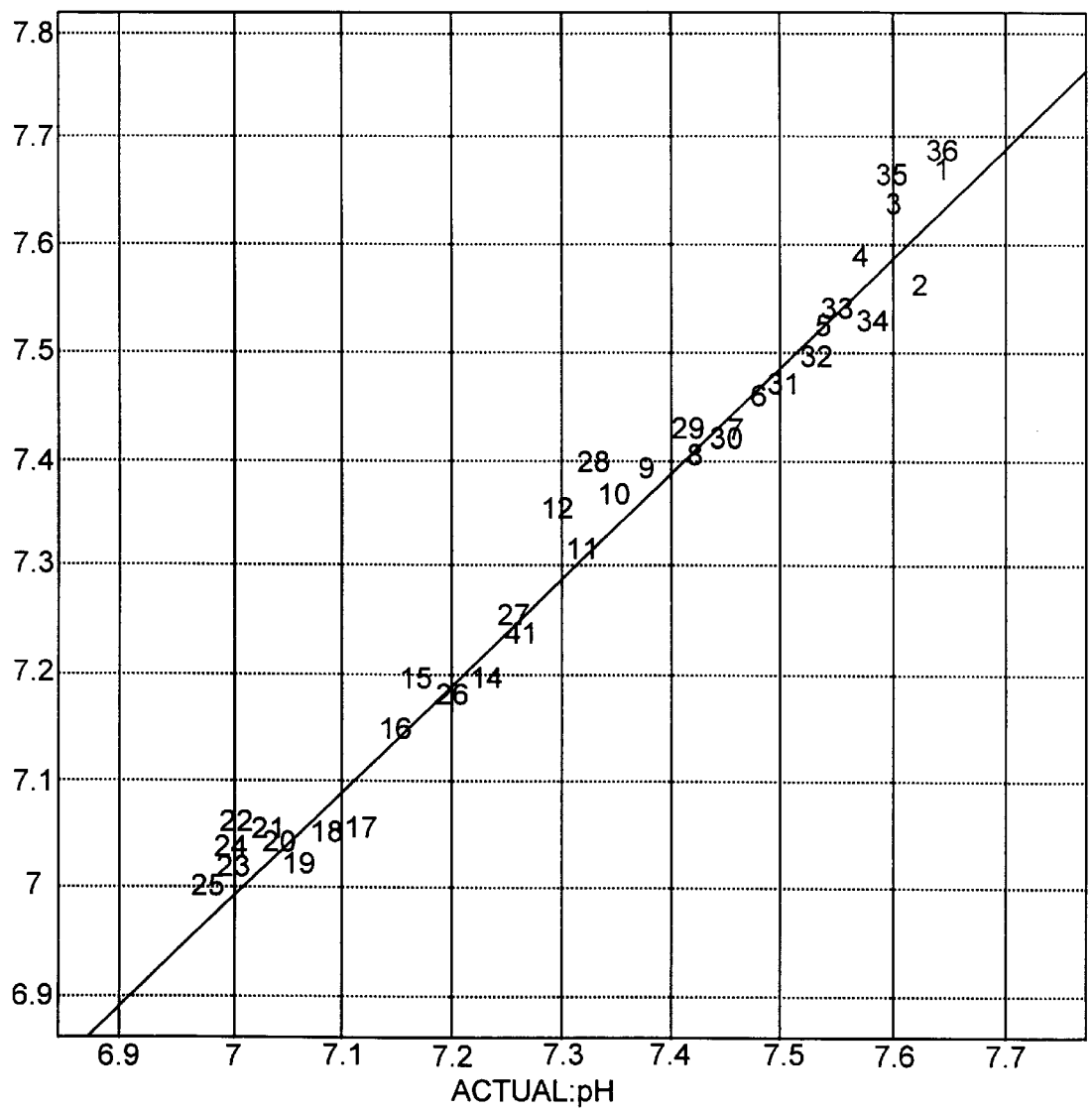
FIG. 15 is a graph of the predicted pH plotted as a function of the actual pH determined for the bare muscle of a rabbit using a model derived from the reflection spectra of FIG. 12.

FIG. 15 is a predicted vs. actual plot of pH for the model derived from the spectroscopic data shown in FIG. 12. 36 data points were used to generate this model. As is clear from the plot, the model fits the data quite well: $R^2$ for the plot is 0.976, while the RMSD is 0.033 pH units. The average error corresponding to this model was 0.03 pH units. The wavelength range used in the model was 700 nm–1250 nm. At these wavelengths, radiation penetration into the muscle is several millimeters, allowing deep muscle pH to be measured.

Figure 16:
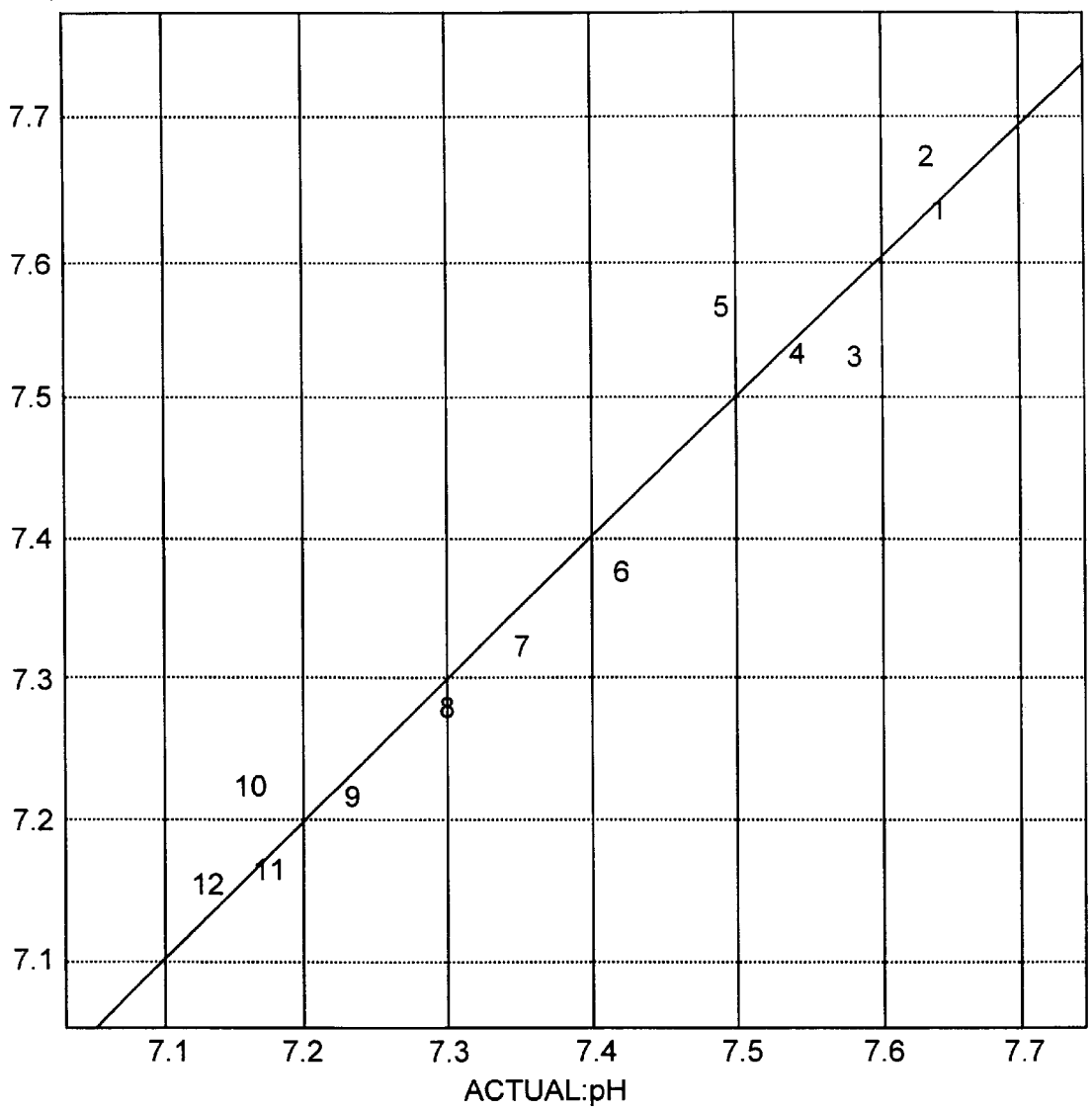
FIG. 16 is a graph of the predicted pH plotted as a function of the actual pH determined for the skin-covered muscle of a rabbit using a model derived from the spectra of FIG. 13; and, FIGS. 17A and 17B are, respectively, a Table comparing model statistics from two different wavelength regions, and a Table showing the results of the mathematical models derived from reflection spectra taken from skin-covered muscles of 5 separate rabbits.

FIG. 16 is a predicted vs. actual plot of pH for a model generated from 12 data points taken using the spectroscopic data of FIG. 13. Here, the model was constructed using wavelengths between 400 nm and 2000 nm. The model had an $R^2$ value of 0.96 and an RMSD of 0.037 pH units, corresponding to an error of 0.04 pH units.

The results from FIGS. 11–16 were used to compare the Ocean Optics and Near IR Systems spectrometers in terms of the model parameters $R^2$ and RMSD. The mean $R^2$ for data collected on the Ocean Optics spectrometer was 0.890±0.072, while the $R^2$ for the Near IR Systems data was 0.960±0.038. Analysis of variance showed that the Near IR Systems data was significantly better (p=0.022, where p is the probability value indicating that the difference in actual and predicted pH is not due to chance). RMSD values for the Ocean Optics spectrometer (0.047±0.032 pH units) and the Near IR Systems (0.035±0.026 pH units) were not significantly different.

In a separate set of experiments, optical spectra and mathematical models were determined from an additional five rabbits (rabbits 10J–14J). In these cases, a skin flap was left covering the latissimus dorsi muscle flap. In these experiments the mean $R^2$ for the 700–1100 nm range, 0.984±0.011, was higher than the value of 0.972±0.025 for the 400–2000 nm range (i.e., the "full range"). Similarly, the RMSD values for the 700–1100 nm range model were 0.016±0.006 pH units, compared to 0.020±0.007 pH units for the full-wavelength range. The results of these studies for rabbits 10J–14J are shown in FIG. 17A.

The wavelength region of 700–1100 nm was used to measure the actual prediction error for the determined models. To provide additional verification of the model, ten percent of the samples were removed before determining the model. The reduced-set model was then used to calculate the pH of remaining samples using the spectra alone. FIG. 17B shows a Table listing the average prediction error for six different experiments using the five rabbits, and the pH values determined from the models. For these six studies, the average error for measuring pH with 200 wavelengths between 700–1100 nm is −0.006±0.009 pH units.

In a separate experiment, the effect of changing the probe height above the rabbit's muscle was studied. As the pH was lowered by ligation, 17 data points were collected from a probe positioned 2.5 mm above the muscle surface, 9 data points were collected at 4.5 mm above the surface, and 6 data points were collected at 1.5 mm from the surface. The first model was derived using only the 17 points collected from the 2.5 mm position. Using that model to predict the points collected at the other heights resulted in an error of 0.151 pH units. A second model was derived using all the points except one point at each height. That model was used to predict the pH of the omitted spectra. That model resulted in an average error of −0.006 pH units for the 3 points. This latter result indicates that calibration models can be developed which are not sensitive to the probe height.

Other embodiments are within the scope of the following claims.

What is claimed is:

1. A non-invasive method for determining the localized pH of a sample tissue disposed underneath a covering tissue of a patient, said method comprising:

irradiating the sample tissue with optical radiation not substantially absorbed by the covering tissue such that the radiation propagates through the covering tissue to irradiate the sample tissue;

collecting radiation from the sample tissue which passes through the covering tissue to determine an optical spectrum; and, processing the optical spectrum and a mathematical model to determine the localized pH of the sample tissue, said model relating optical spectra to known pH values of interstitial fluid in tissue.

2. The method of claim 1, wherein said processing includes comparing the optical spectrum to the mathematical model to determine the pH of the sample tissue.

3. A method of claim 1, wherein the covering tissue is skin.

4. A method of claim 1, wherein the optical radiation is infrared radiation.

5. A method of claim 4, wherein the infrared radiation is between 700 nm and 1100 nm.

6. A method of claim 1, wherein the mathematical model is determined prior to said irradiating by collecting multiple optical spectra, each occurring at a known pH value, from a representative sample, and then processing the optical spectra and known pH values with a mathematical algorithm to determine the model.

7. A method of claim 6, wherein the mathematical algorithm is a partial least-squares fitting algorithm.

8. A method of claim 6, wherein the model comprises a linear or non-linear mathematical equation relating pH to the reflectivity or absorptivity of the sample tissue.

9. A method of claim 6, wherein the representative sample is a sample tissue of the patient.

10. A method of claim 6, wherein the representative sample is a solution or a second tissue.

11. A method of claim 1, wherein the sample tissue comprises muscle or organ.

12. A method of claim 1, wherein the localized pH is in a pH range of about 5.8 to 7.6.

13. A method of claim 1, further including determining a level of ischemia of the sample tissue from said localized pH.

14. A method of claim 1, wherein said step of collecting radiation from the sample tissue comprises collecting radiation reflected from the sample tissue.

15. A method of claim 1, wherein the optical radiation is between 400 nm and 2000 nm.

16. A method for determining the localized pH of a sample tissue, said method comprising:
   irradiating the sample tissue with optical radiation;
   collecting radiation from the sample tissue to determine an optical spectrum; and,
   processing the optical spectrum and a mathematical model to determine the localized pH of the sample tissue, said model relating optical spectra to known pH values of interstitial fluid in tissue.

17. A method of claim 16, wherein the mathematical model is determined prior to said irradiating by collecting multiple optical spectra, each occurring at a known pH value, from a representative sample, and then processing the optical spectra and known pH values with a mathematical algorithm to determine the model.

18. A method of claim 17, wherein the representative sample is a sample tissue of the patient.

19. A method of claim 17, wherein the representative sample is a solution or a second tissue.

20. A method of claim 16, wherein the step of irradiating the sample tissue with optical radiation includes invasively accessing the sample tissue to irradiate the sample tissue.

21. A method of claim 20, wherein the sample tissue is accessed with an endoscope.

22. A method of claim 16, further including determining a level of ischemia of the sample tissue from said localized pH.

23. A device for determining the pH of a sample, said device comprising:
   an array of light sources for delivering radiation to the sample, wherein each of said light sources delivers radiation at a unique set of optical wavelengths;
   a power supply;
   a modulation system in electrical contact with each of said light sources and said power supply, said modulation system configured to modulate electrical power delivered from said power supply to each of said light sources at a unique frequency;
   a detection system comprising a first optical detector configured to receive radiation delivered from each light source and from the sample, said detection system, after receiving radiation from the sample, generating a first set of radiation-induced electrical signals, each corresponding to radiation delivered from a separate light source, said detection system further including phase-sensitive detection electronics in electrical contact with said first optical detector to detect radiation generated at the unique frequency, said phase-sensitive detection electronics being incorporated in a lock-in amplifier;
   a signal processor for receiving the first set of electrical signals and, in response, generating a first set of digital electrical signals; and,
   a microprocessor configured to receive the first set of digital electrical signals to calculate the pH of the sample, said microprocessor being programmed to first process the first set of digital electrical signals to determine a first spectrum and then compare the first spectrum or a spectrum determined from the first spectrum to a mathematical model to determine the pH of the sample.

24. A device of claim 23, wherein said microprocessor is additionally programmed to calculate the mathematical model prior to processing the first set of digital electrical signals.

25. A device of claim 23, wherein said device further comprises a lens configured to focus radiation from said light sources into a fiber optic cable.

26. A device of claim 25, wherein said fiber optic cable comprises a delivery fiber for delivering radiation to the sample, and a signal fiber for delivering radiation reflected by the sample to said first optical detector.

27. A device of claim 23, wherein said light sources deliver infrared wavelengths.

28. A device of claim 27, wherein the infrared wavelengths are between 700 nm and 1100 nm.

29. A device of claim 27, wherein each light source delivers infrared radiation having a bandwidth of between about 10 and 100 nm.

30. A device of claim 23, wherein each light source is a light-emitting diode.

31. A device of claim 23, wherein each light source is a diode laser.

32. A device of claim 23, wherein said array of light sources comprises between 2 and 20 light sources.

33. A device of claim 23, wherein said detection system comprises a second optical detector configured to detect radiation directly from each of said light sources, said second optical detector, in response to the radiation, generating a second set of radiation-induced electrical signals, each corresponding to radiation delivered from a separate light source.

34. A device of claim 33, wherein said signal processor is additionally configured for receiving the second set of electrical signals and, in response, generating a second set of digital electrical signals.

35. A device of claim 34, wherein said microprocessor is additionally programmed to process the second set of digital electrical signals to determine a reference spectrum and then calculate a ratio between the reference spectrum and the first spectrum.

36. A device of claim 33, wherein said device further comprises a reference fiber for delivering radiation from said light sources to said second optical detector.

37. A device of claim 23, wherein said radiation from the sample comprises reflected radiation.

38. A portable device for determining the pH of a sample, said device comprising:
   a mount having a series of holes extending therethrough;
   an array of light sources attached to said mount and positioned to deliver radiation to the sample through said series of holes;
   a power supply electrically coupled to said mount;
   a modulation system electrically coupled to said mount and arranged to modulate electrical power delivered from said power supply to each of said light sources;
   a detection system comprising a first optical detector attached to said mount and positioned to receive radiation from the sample, said detection system, after receiving sample radiation, generating a first set of electrical signals, each corresponding to sample radiation delivered from a separate light source and received from the sample;
   a signal processor electrically coupled to said mount for receiving the first set of electrical signals and, in response, generating a first set of digital signals; and
   a microprocessor configured to receive the first set of digital signals and to calculate the pH of the sample, said microprocessor being programmed to process the first set of digital signals to determine a sample spectrum and then compare the sample spectrum to a mathematical model to determine the pH of the sample.

39. A device of claim 38, wherein said power supply, said modulation system, said signal processor, and said microprocessor are attached to said mount.

40. A device of claim 38, wherein said array of light sources are positioned such that said radiation delivered by each said light source is aimed at a common spot on a tissue sample.

41. A device of claim 38, wherein said first optical detector is located on an outer, tissue facing surface of said mount.

42. A device of claim 38, wherein said detection system comprises a second optical detector arranged to detect reference radiation directly from each of said light sources, said second optical detector, in response to the radiation, generating a second set of electrical signals, each corresponding to reference radiation delivered from a separate light source.

43. A device of claim 42, wherein said second optical detector is located on an inner, non-tissue facing surface of said mount.

44. A device of claim 42, wherein said mount comprises a mounting plate comprising said series of holes and a cover attached to said mounting plate, said array of light sources being attached to said cover, said cover including a reflective surface arranged to reflect radiation from each of said light sources to said second optical detector.

45. A device of claim 42, wherein said signal processor receives the second set of electrical signals and, in response, generates a second set of digital signals, said microprocessor being additionally programmed to process the second set of digital reference signals to determine a reference spectrum and then calculate a ratio between the reference spectrum and the sample spectrum.

46. A device of claim 39, wherein said array of light sources are evenly spaced and arranged in a circular pattern, and said series of holes are evenly spaced and arranged in a circular pattern.

47. A method for determining the localized pH of a sample tissue, said method comprising:
   irradiating the sample tissue with optical radiation;
   collecting radiation from the sample tissue to determine an optical spectrum; and,
   processing the optical spectrum and a mathematical model to determine the localized pH of the sample tissue, said model relating optical spectra to known pH values of muscle or organ cells.

48. A portable device for determining the pH of a sample, said device comprising:
   a mount;
   an array of light sources attached to said mount;
   a fiber optic cable attached to said mount, said fiber optic cable including a delivery fiber for delivering radiation to the sample, a reference fiber, and a signal fiber;
   a lens attached to said mount, said lens configured to focus radiation from said light sources into said fiber optic cable,
   a power supply electrically coupled to said mount;
   a modulation system electrically coupled to said mount and arranged to modulate electrical power delivered from said power supply to each of said light sources;
   a detection system comprising a first optical detector attached to said mount and coupled to said signal fiber for receiving radiation from the sample, said detection system, after receiving sample radiation, generating a first set of electrical signals, each corresponding to sample radiation delivered from a separate light source and received from the sample, and a second optical detector attached to said mount and coupled to said reference fiber for receiving radiation directly from each of said light sources, said second optical detector, in response to the radiation, generating a second set of radiation-induced electrical signals, each corresponding to radiation delivered from a separate light source;
   a signal processor electrically coupled to said mount for receiving the first set of electrical signals and, in response, generating a first set of digital signals, and for receiving the second set of electrical signals and, in response, generating a second set of digital electrical signals; and
   a microprocessor configured to receive the first set and the second set of digital signals and to calculate the pH of the sample, said microprocessor being programmed to process the first set of digital signals to determine a sample spectrum and then compare the sample spectrum to a mathematical model to determine the pH of the sample, said microprocessor additionally being programmed to process the second set of digital electrical signals to determine a reference spectrum and then calculate a ratio between the reference spectrum and the first spectrum.

49. A device of claim 48, wherein said power supply, said modulation system, said signal processor, and said microprocessor are attached to said mount.

50. A device of claim 48, wherein at least a portion of said fiber optic cable comprises a delivery fiber surrounded by radially and symmetrically disposed fibers.

51. A device of claim 50, wherein said delivery fiber is surrounded by radially and symmetrically disposed reference fibers in the region where said fiber optic cable receives radiation from said light sources.

52. A device of claim 50, wherein said delivery fiber is surrounded by radially and symmetrically disposed signal fibers in the region where said fiber optic cable delivers radiation to the sample.

53. A device of claim 48, wherein said array of light sources is arranged on said mount such that incident irradiation irradiates said lens in a symmetric, ring-like pattern disposed radially around a center of said lens.

54. A device of claim 48, further comprising a housing attached to said mount, said lens being supported by said housing.

* * * * *